United States Patent
Kautz et al.

(10) Patent No.: US 7,632,844 B2
(45) Date of Patent: *Dec. 15, 2009

(54) 2-HYDROXY-6-PHENYLPHENANTHRIDINES AS PDE-4 INHIBITORS

(75) Inventors: Ulrich Kautz, Allensbach (DE); Beate Schmidt, Allensbach (DE)

(73) Assignee: Nycomed GmbH, Constance (DE)

(*) Notice: Subject to any disclaimer, the term of this patent is extended or adjusted under 35 U.S.C. 154(b) by 45 days.

This patent is subject to a terminal disclaimer.

(21) Appl. No.: 12/000,710

(22) Filed: Dec. 17, 2007

(65) Prior Publication Data
US 2008/0319067 A1     Dec. 25, 2008

Related U.S. Application Data

(63) Continuation of application No. 10/524,819, filed as application No. PCT/EP03/09547 on Aug. 28, 2003, now Pat. No. 7,329,676.

(30) Foreign Application Priority Data
Aug. 29, 2002 (EP) .................................. 02019335

(51) Int. Cl.
*A61K 31/473* (2006.01)
*A61K 31/4741* (2006.01)

(52) U.S. Cl. ....................... 514/298; 514/287

(58) Field of Classification Search ................. 514/298, 514/287
See application file for complete search history.

(56) References Cited

U.S. PATENT DOCUMENTS

| 6,121,279 | A | 9/2000 | Gutterer |
| 6,127,378 | A | 10/2000 | Gutterer |
| 6,191,138 | B1 | 2/2001 | Gutterer |
| 6,410,551 | B1 | 6/2002 | Gutterer |
| 7,329,676 | B2 * | 2/2008 | Kautz et al. ............ 514/298 |
| 2005/0239818 | A1 | 10/2005 | Kautz |
| 2007/0167482 | A1 | 7/2007 | Kautz |
| 2007/0185149 | A1 | 8/2007 | Kautz |
| 2007/0191413 | A1 | 8/2007 | Kautz |
| 2007/0191414 | A1 | 8/2007 | Kautz |
| 2007/0259909 | A1 | 11/2007 | Kautz |

FOREIGN PATENT DOCUMENTS

| EP | 0490823 A1 | 6/1992 |
| WO | 9728131 A1 | 8/1997 |
| WO | 9735854 A1 | 10/1997 |
| WO | 9905111 A1 | 2/1999 |
| WO | 9905112 A1 | 2/1999 |
| WO | 9905113 A1 | 2/1999 |
| WO | 9957118 A1 | 11/1999 |
| WO | 0042018 A1 | 7/2000 |
| WO | 0042020 A1 | 7/2000 |
| WO | 0205616 A1 | 1/2002 |
| WO | 0206238 A1 | 1/2002 |
| WO | 2004019945 A1 | 3/2004 |

OTHER PUBLICATIONS

Souness et al., "Immunosuppressive and anti-inflammatory effects of cyclic AMP phosphodiesterase (PDE) type 4 inhibitors," Immunopharmacology, vol. 47, pp. 127-162 (2000).
Montana et al., "Chapter 5. Phosphodiesterase 4 Inhibitors," Annual Reports in Medicinal Chemistry, vol. 36, pp. 47-56 (2001).
Schmidt et al., "The phosphodiesterase 4 inhibitor roflumilast is effective in the treatment of allergic rhinitis," J. Allergy Clin. Immunol., vol. 108, No. 4, pp. 530-536 (2001).
Dyke et al., "Update on the therapeutic potential of PDE4 inhibitors," Expert Opin. Investig. Drugs, vol. 11, No. 1, pp. 1-13 (2002).
"Highly Selective Phosphodiesterase 4 Inhibitors for the Treatment of Allergic Skin Diseases and Psoriasis", Baumer et al., *Inflammation and Allergy—Drug Targets*, vol. 6, pp. 17-26 (2006).

* cited by examiner

*Primary Examiner*—Charanjit S Aulakh
(74) *Attorney, Agent, or Firm*—The Nath Law Group; Joshua B. Goldberg; Sheldon M. McGee

(57) ABSTRACT

The compounds of formula I

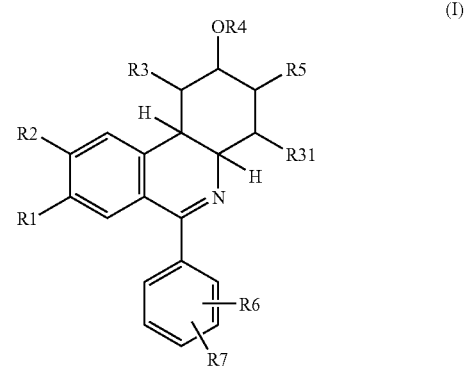

in which R1, R2, R3, R31, R4, R5, R6 and R7 have the meanings as indicated in the description, are novel effective PDE4 inhibitors.

13 Claims, No Drawings

2-HYDROXY-6-PHENYLPHENANTHRIDINES AS PDE-4 INHIBITORS

This application is a continuation of U.S. Ser. No. 10/524,819, filed Feb. 18, 2005 now U.S. Pat. No. 7,329,676, which was filed under 35 U.S.C. 371 as a national stage of PCT/EP03/09547, filed Aug. 28, 2003.

FIELD OF APPLICATION OF THE INVENTION

The invention relates to novel 2-hydroxy-6-phenylphenanthridines, which are used in the pharmaceutical industry for the production of pharmaceutical compositions.

KNOWN TECHNICAL BACKGROUND

The international applications WO 97/28131 (=U.S. Pat. No. 6,191,138), WO 97/35854 (=U.S. Pat. No. 6,127,378), WO 99/05113 (=U.S. Pat. No. 6,121,279), WO99/05111 (=U.S. Pat. No. 6,410,551), WO 00/42018, WO 00/42020, WO 02/05616 and WO 02/06238 describe 6-phenylphenanthridines as PDE4 inhibitors.

DESCRIPTION OF THE INVENTION

It has now been found that the novel 2-hydroxy-6-phenylphenanthridines described in greater detail below differ from the previously known 6-phenylphenanthridines by unanticipated and sophisticated structural alterations and have surprising and particularly advantageous properties.

The invention thus relates to compounds of the formula I,

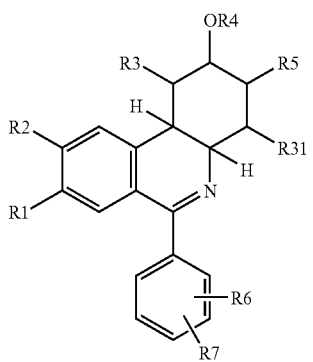

(I)

in which
R1 is hydroxyl, 1-4C-alkoxy, 3-7C-cycloalkoxy, 3-7C-cycloalkylmethoxy, or completely or predominantly fluorine-substituted 1-4C-alkoxy,
R2 is hydroxyl, 1-4C-alkoxy, 3-7C-cycloalkoxy, 3-7C-cycloalkylmethoxy, or completely or predominantly fluorine-substituted 1-4C-alkoxy,
or in which
R1 and R2 together are a 1-2C-alkylenedioxy group,
R3 is hydrogen or 1-4C-alkyl,
R31 is hydrogen or 1-4C-alkyl,
R4 is hydrogen, 1-4C-alkyl, completely or predominantly fluorine-substituted 1-4C-alkyl, 1-4C-alkoxy-1-4C-alkyl, hydroxy-2-4C-alkyl or 1-7C-alkylcarbonyl,
R5 is hydrogen or 1-4C-alkyl,
R6 is hydrogen, 1-4C-alkyl, trifluoromethyl, 1-4C-alkoxy, completely or predominantly fluorine-substituted 1-4C-alkoxy, 3-7C-cycloalkoxy, 3-7C-cycloalkylmethoxy, halogen, nitro, cyano, hydroxyl, 1-4C-alkylcarbonyloxy, amino, mono- or di-1-4C-alkylamino, phenyl, phenyl-1-4C-alkyl, 1-4C-alkylcarbonylamino, phenoxy or C(O)OR61, wherein
R61 is hydrogen, 1-7C-alkyl, 3-7C-cycloalkyl or 3-7C-cycloalkylmethyl,
R7 is hydrogen, 1-4C-alkyl, hydroxyl, halogen, 1-4C-alkoxy, completely or predominantly fluorine-substituted 1-4C-alkoxy, 3-7C-cycloalkoxy, 3-7C-cycloalkylmethoxy or C(O)OR61, and the salts, the N-oxides and the salts of the N-oxides of these compounds.

1-4C-Alkyl represents a straight-chain or branched alkyl radical having 1 to 4 carbon atoms. Examples which may be mentioned are the butyl, isobutyl, sec-butyl, tert-butyl, propyl, isopropyl and preferably the ethyl and methyl radicals.

1-7C-Alkyl represents a straight-chain or branched alkyl radical having 1 to 7 carbon atoms. Examples which may be mentioned are the heptyl, isoheptyl (5-methylhexyl), hexyl, isohexyl (4-methylpentyl), neo-hexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl or methyl radicals.

1-4C-Alkoxy represents radicals which, in addition to the oxygen atom, contain a straight-chain or branched alkyl radical having 1 to 4 carbon atoms. Examples which may be mentioned are the butoxy, iso-butoxy, sec-butoxy, tert-butoxy, propoxy, isopropoxy and preferably the ethoxy and methoxy radicals.

3-7C-Cycloalkoxy represents cyclopropyloxy, cyclobutyloxy, cyclopentyloxy, cyclohexyloxy and cyclo-heptyloxy, of which cyclopropyloxy, cyclobutyloxy and cyclopentyloxy are preferred.

3-7C-Cycloalkylmethoxy represents cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

As completely or predominantly fluorine-substituted 1-4C-alkoxy, for example, the 2,2,3,3,3-pentafluoropropoxy, the perfluoroethoxy, the 1,2,2-trifluoroethoxy, in particular the 1,1,2,2-tetrafluoroethoxy, the 2,2,2-trifluoroethoxy, the trifluoromethoxy and preferably the difluoromethoxy radicals may be mentioned. "Predominantly" in this connection means that more than half of the hydrogen atoms of the 1-4C-alkoxy radicals are replaced by fluorine atoms.

As completely or predominantly fluorine-substituted 1-4C-alkyl, for example, the 2,2,3,3,3-pentafluoro-propyl, the perfluoroethyl, the 1,2,2-trifluoroethyl, in particular the 1,1,2,2-tetrafluoroethyl, the 2,2,2-trifluoroethyl, the trifluoromethyl and preferably the difluoromethyl radicals may be mentioned. "Predominantly" in this connection means that more than half of the hydrogen atoms of the 1-4C-alkyl radicals are replaced by fluorine atoms.

1-2C-Alkylenedioxy represents, for example, the methylenedioxy [—O—CH$_2$—O—] and the ethylenedioxy [—O—CH$_2$—CH$_2$—O—] radicals.

1-4C-Alkoxy-1-4C-alkyl represents one of the abovementioned 1-4C-alkyl radicals, which is substituted by one of the abovementioned 1-4C-alkoxy radicals. Examples which may be mentioned are the methoxymethyl, the methoxyethyl and the isopropoxyethyl radicals, particularly the 2-methoxyethyl and the 2-isopropoxyethyl radicals.

1-4C-Alkylcarbonyl represents a radical which, in addition to the carbonyl group, contains one of the abovementioned 1-4C-alkyl radicals. An example which may be mentioned is the acetyl radical.

1-7C-Alkylcarbonyl represents a radical which, in addition to the carbonyl group, contains one of the abovementioned 1-7C-alkyl radicals. Examples which may be mentioned are the acetyl, propionyl, butanoyl and hexanoyl radicals.

Hydroxy-2-4C-alkyl represents 2-4C-alkyl radicals, which are substituted by a hydroxyl group. Examples which may be mentioned are the 2-hydroxyethyl and the 3-hydroxypropyl radicals.

In addition to the nitrogen atom, mono- or di-1-4C-alkylamino radicals contain one or two of the abovementioned 1-4C-alkyl radicals. Di-1-4C-alkylamino is preferred and here, in particular, dimethyl-, diethyl- or diisopropylamino.

Halogen within the meaning of the invention is bromine, chlorine or fluorine.

3-7C-Cycloalkyl represents cyclopropyl, cyclobutyl, cyclopentyl, cyclohexyl and cycloheptyl, of which cyclopropyl, cyclobutyl and cyclopentyl are preferred.

3-7C-Cycloalkylmethyl represents a methyl radical which is substituted by one of the abovementioned 3-7C-cycloalkyl radicals. Preferably, the 3-5C-cycloalkylmethyl radicals cyclopropylmethyl, cyclobutylmethyl and cyclopentylmethyl may be mentioned.

Phenyl-1-4C-alkyl represents one of the abovementioned, phenyl-substituted 1-4C-alkyl radicals. Examples which may be mentioned are the phenethyl and the benzyl radicals.

1-4C-Alkylcarbonyloxy represents a carbonyloxy group to which one of the abovementioned 1-4C-alkyl radicals is bonded. An example which may be mentioned is the acetoxy radical [CH$_3$C(O)—O—].

1-4C-Alkylcarbonylamino represents an amino radical which is substituted by one of the abovementioned 1-4C-alkylcarbonyl radicals. An example which may be mentioned is the acetamido radical [CH$_3$C(O)—NH—].

Exemplary phenyl radicals substituted by R6 and R7 which may be mentioned are the radicals 4-acetamidophenyl, 3-acetamidophenyl, 4-acetoxyphenyl, 3-aminophenyl, 4-aminophenyl, 2-bromophenyl, 4-bromophenyl, 2-chlorophenyl, 3-chlorophenyl, 4-chlorophenyl, 3-bromophenyl, 2,3-dichlorophenyl, 2,4-dichlorophenyl, 2-chloro-4-nitrophenyl, 4-diethylamino-2-methylphenyl, 4-methoxyphenyl, 3-methoxyphenyl, 2-chloro-5-nitrophenyl, 4-chloro-3-nitrophenyl, 2,6-dichlorophenyl, 3,5-dichlorophenyl, 2,5-dichlorophenyl, 2,6-dibromophenyl, 2-cyanophenyl, 3-cyanophenyl, 4-cyanophenyl, 4-diethylaminophenyl, 4-dimethylaminophenyl, 2-fluorophenyl, 4-fluorophenyl, 3-fluorophenyl, 2,4-difluorophenyl, 2,6-difluorophenyl, 2-chloro-6-fluorophenyl, 2-fluoro-5-nitrophenyl, 2-hydroxyphenyl, 3-hydroxyphenyl, 3,4-dichlorophenyl, 4-hydroxyphenyl, 4-hydroxy-3-methoxyphenyl, 2-hydroxy-4-methoxyphenyl, 2,4-dihydroxyphenyl, 2-methoxyphenyl, 2,3-dimethoxyphenyl, 3,4-dimethoxyphenyl, 2,4-dimethoxyphenyl, 3-dimethylaminophenyl, 2-dimethylaminophenyl, 2-methylphenyl, 3-methylphenyl, 4-methylphenyl, 2-chloro-6-methylphenyl, 4-methyl-3-nitrophenyl, 2,4-dimethylphenyl, 2,6-dimethylphenyl, 2,3-dimethylphenyl, 2-nitrophenyl, 3-nitrophenyl, 4-nitrophenyl, 4-ethoxyphenyl, 2-trifluoromethylphenyl, 4-trifluoromethylphenyl, 3-trifluoromethylphenyl, 4-benzylphenyl, 4-biphenyl, 4-trifluoromethoxyphenyl, 3-trifluoromethoxyphenyl, 2-trifluoromethoxyphenyl, 3-cyclopentyloxyphenyl, 4-cyclopentyloxyphenyl, 4-cyclohexyloxyphenyl, 3-cyclohexyloxyphenyl, 3-cyclopropylmethoxyphenyl, 4-cyclopropylmethoxyphenyl, 3-cyclopropylmethoxy-4-methoxyphenyl, 3-cyclopropylmethoxy-4-difluoromethoxyphenyl, 3-cyclopropylmethoxy-4-ethoxyphenyl, 4-cyclopropylmethoxy-3-methoxyphenyl, 3-cyclopropylmethoxy-5-methoxyphenyl, bis-3,4-cyclopropylmethoxyphenyl, bis-3,5-cyclopropylmethoxyphenyl, 3,4-dicyclopentyloxyphenyl, 3-cyclopentyloxy-4-methoxyphenyl, 4-cyclopentyloxy-3-methoxyphenyl, 3-cyclopropylmethoxy-4-cyclopentyloxyphenyl, 3-cyclopentyloxy-5-methoxyphenyl, 4-cyclopropylmethoxy-3-cyclopentyloxyphenyl, 3-cyclobutyloxy-4-methoxyphenyl, 3-cyclopropylmethoxy-4-acetylaminophenyl, 4-carboxyphenyl, 4-methoxycarbonylphenyl, 4-ethoxycarbonylphenyl, 4-isopropoxycarbonylphenyl, 3-carboxyphenyl, 3-methoxycarbonylphenyl, 3-ethoxycarbonylphenyl, 3-isopropoxycarbonylphenyl, 4-methoxycarbonyl-3-methylphenyl, 3-chloro-4-methoxycarbonylphenyl, 3-bromo-4-methoxycarbonylphenyl, 3-fluoro-4-methoxycarbonylphenyl, 3-hydroxy-4-methoxycarbonylphenyl, 2-chloro-4-methoxycarbonylphenyl, 2-bromo-4-methoxycarbonylphenyl, 2-fluoro-4-methoxycarbonylphenyl, 2-methoxy-4-methoxycarbonylphenyl, 4-methoxycarbonyl-2-methylcarbonylphenyl, 4-fluoro-3-methoxycarbonylphenyl, 4-ethoxy-3-methoxycarbonylphenyl, 4-methoxy-3-methoxycarbonylphenyl, 4-isopropoxy-3-methoxycarbonylphenyl, 3-methoxycarbonyl-4-methylphenyl, 5-tert-butyl-3-methoxycarbonylphenyl, 3-methoxycarbonyl-5-methylphenyl, 3-bromo-5-methoxycarbonylphenyl, 3-chloro-5-methoxycarbonylphenyl, 3-methoxy-5-methoxycarbonylphenyl, 3-acetoxy-4-methoxycarbonylphenyl, 4-methoxycarbonyl-2-nitrophenyl, 4-methoxycarbonyl-2-phenylphenyl, 2-cyano-4-methoxycarbonylphenyl, 4-acetoxy-3-methoxycarbonylphenyl, 3-methoxycarbonyl-4-nitrophenyl, 3-methoxycarbonyl-5-phenylphenyl, 5-cyano-3-methoxycarbonylphenyl, 5-methoxycarbonyl-3-nitrophenyl, 4-methoxy-3-propoxy-phenyl, 4-butoxyphenyl, 4-difluoromethoxyphenyl, 3-difluoromethoxyphenyl, 3,4-bis-difluoromethoxyphenyl, 4-(1,1,2,2-tetrafluoroethoxy)-phenyl, 3-fluoro-4-methoxyphenyl or 4-phenoxyphenyl.

Possible salts for compounds of the formula I—depending on substitution—are all acid addition salts or all salts with bases. Particular mention may be made of the pharmacologically tolerable salts of the inorganic and organic acids and bases customarily used in pharmacy. Those suitable are, on the one hand, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, it being possible to employ the acids in salt preparation—depending on whether a mono- or polybasic acid is concerned and depending on which salt is desired—in an equimolar quantitative ratio or one differing therefrom.

On the other hand, salts with bases are also suitable. Examples of salts with bases which may be mentioned are alkali metal (lithium, sodium, potassium) or calcium, aluminum, magnesium, titanium, ammonium, meglumine or guanidinium salts, where here too the bases are employed in salt preparation in an equimolar quantitative ratio or one differing therefrom.

Pharmacologically intolerable salts which can initially be obtained, for example, as process products in the preparation of the compounds according to the invention on an industrial scale are converted into pharmacologically tolerable salts by processes known to the person skilled in the art.

It is known to the person skilled in the art that the compounds according to the invention and their salts, when they are isolated, for example, in crystalline form, can contain various amounts of solvents. The invention therefore also comprises all solvates and in particular all hydrates of the compounds of the formula I, and also all solvates and in particular all hydrates of the salts of the compounds of the formula I.

The substituents R6 and R7 of compounds of formula I can be attached in the ortho, meta or para position with respect to the binding position in which the 6-phenyl ring is bonded to the phenanthridine ring system, whereby preference is given to the attachment in the meta or, particularly, in the para position.

An embodiment (embodiment a) of the invention are compounds of the formula I in which
R1 is 1-2C-alkoxy, 3-5C-cycloalkoxy, 3-5C-cycloalkylmethoxy, or completely or predominantly fluorine-substituted 1-2C-alkoxy,
R2 is 1-2C-alkoxy, 3-5C-cycloalkoxy, 3-5C-cycloalkylmethoxy, or completely or predominantly fluorine-substituted 1-2C-alkoxy,
R3 is hydrogen,
R31 is hydrogen,
R4 is hydrogen, 1-4C-alkyl, 1-2C-alkoxy-2-4C-alkyl or 1-7C-alkylcarbonyl,
R5 is hydrogen,
R6 is 1-4C-alkyl, 1-4C-alkoxy, completely or predominantly fluorine-substituted 1-4C-alkoxy, 3-7C-cycloalkylmethoxy, halogen, nitro, cyano, hydroxyl, 1-4C-alkylcarbonyloxy, mono- or di-1-4C-alkylamino, 1-4C-alkylcarbonylamino, phenoxy or C(O)OR61, wherein
R61 is hydrogen or 1-7C-alkyl,
R7 is hydrogen, halogen, 1-4C-alkoxy, completely or predominantly fluorine-substituted 1-4C-alkoxy, or 3-7C-cycloalkylmethoxy, and the salts, the N-oxides and the salts of the N-oxides of these compounds.

Compounds of embodiment a, which are to be emphasized, are those compounds of the formula I in which
R1 is 1-2C-alkoxy, or completely or predominantly fluorine-substituted 1-2C-alkoxy,
R2 is 1-2C-alkoxy, or completely or predominantly fluorine-substituted 1-2C-alkoxy,
R3 is hydrogen,
R31 is hydrogen,
R4 is hydrogen, 1-4C-alkyl, 1-2C-alkoxyethyl or 1-7C-alkylcarbonyl,
R5 is hydrogen,
R6 is 1-4C-alkyl, 1-4C-alkoxy, completely or predominantly fluorine-substituted 1-4C-alkoxy, 3-7C-cycloalkylmethoxy, halogen, nitro, cyano; hydroxyl, 1-4C-alkylcarbonyloxy, mono- or di-1-4C-alkylamino, 1-4C-alkylcarbonylamino, phenoxy or C(O)OR61, wherein
R61 is hydrogen or 1-7C-alkyl,
R7 is hydrogen, halogen, 1-4C-alkoxy, completely or predominantly fluorine-substituted 1-4C-alkoxy, or 3-7C-cycloalkylmethoxy, and the salts, the N-oxides and the salts of the N-oxides of these compounds.

Compounds of embodiment a, which are in particular to be emphasized, are those compounds of the formula I in which
R1 is methoxy or difluoromethoxy,
R2 is methoxy, difluoromethoxy or ethoxy,
R3 is hydrogen,
R31 is hydrogen,
R4 is hydrogen, methyl, ethyl, methoxyethyl or acetyl,
R5 is hydrogen,
R6 is methyl, methoxy, ethoxy, propoxy, butoxy, difluoromethoxy, trifluoromethoxy, 1,1,2,2-tetrafluoroethoxy, cyclopropylmethoxy, fluorine, chlorine, bromine, nitro, cyano, hydroxyl, acetoxy, dimethylamino, acetamido, phenoxy or C(O)OR61, wherein
R61 is hydrogen or methyl,
R7 is hydrogen, fluorine, methoxy, ethoxy, propoxy, butoxy, difluoromethoxy or cyclopropylmethoxy, and the salts, the N-oxides and the salts of the N-oxides of these compounds.

Compounds of embodiment a, which are in more particular to be emphasized, are those compounds of the formula I in which
R1 is methoxy, and
R2 is methoxy,
or
R1 is difluoromethoxy, and
R2 is methoxy,
or
R1 is methoxy, and
R2 is ethoxy or difluoromethoxy,
R3 is hydrogen,
R31 is hydrogen,
R4 is hydrogen, methyl, ethyl, methoxyethyl or acetyl,
R5 is hydrogen,
R6 is methyl, methoxy, ethoxy, propoxy, butoxy, difluoromethoxy, trifluoromethoxy, 1,1,2,2-tetrafluoroethoxy, cyclopropylmethoxy, fluorine, chlorine, bromine, nitro, cyano, hydroxyl, acetoxy, dimethylamino, acetamido, phenoxy or C(O)OR61, wherein
R61 is hydrogen or methyl,
R7 is hydrogen, fluorine, methoxy, difluoromethoxy or cyclopropylmethoxy, and the salts, the N-oxides and the salts of the N-oxides of these compounds.

A further embodiment (embodiment b) of the invention are compounds of the formula I in which
R1 is hydroxyl, 1-4C-alkoxy, 3-7C-cycloalkoxy, 3-7C-cycloalkylmethoxy or completely or predominantly fluorine-substituted 1-4C-alkoxy,
R2 is hydroxyl, 1-4C-alkoxy, 3-7C-cycloalkoxy, 3-7C-cycloalkylmethoxy or completely or predominantly fluorine-substituted 1-4C-alkoxy,
or in which
R1 and R2 together are a 1-2C-alkylenedioxy group,
R3 is hydrogen or 1-4C-alkyl,
R31 is hydrogen or 1-4C-alkyl,
R4 is hydrogen, 1-4C-alkyl, completely or predominantly fluorine-substituted 1-4C-alkyl, 1-4C-alkoxy-1-4C-alkyl, hydroxy-2-4-alkyl or 1-7C-alkylcarbonyl,
R5 is hydrogen or 1-4C-alkyl,
R6 is hydrogen, 1-4C-alkyl, trifluoromethyl, 1-4C-alkoxy, completely or predominantly fluorine-substituted 1-4C-alkoxy, 3-7C-cycloalkoxy, 3-7C-cycloalkylmethoxy, halogen, nitro, cyano, hydroxyl, 1-4C-alkylcarbonyloxy, amino, mono- or di-1-4C-alkylamino, phenyl, phenyl-1-4C-alkyl, 1-4C-alkylcarbonylamino or C(O)OR61, wherein
R61 is hydrogen, 1-7C-alkyl, 3-7C-cycloalkyl or 3-7C-cycloalkylmethyl,
R7 is hydrogen, 1-4C-alkyl, hydroxyl, halogen, 1-4C-alkoxy, completely or predominantly fluorine-substituted 1-4C-alkoxy, 3-7C-cycloalkoxy, 3-7C-cycloalkylmethoxy or C(O)OR61, and the salts, the N-oxides and the salts of the N-oxides of these compounds.

Compounds of embodiment b, which are to be emphasized, are those compounds of the formula I in which
R1 is 1-2C-alkoxy, 3-5C-cycloalkoxy, 3-5C-cycloalkyl-methoxy or completely or predominantly fluorine-substituted 1-2C-alkoxy,
R2 is 1-2C-alkoxy, 3-5C-cycloalkoxy, 3-5C-cycloalkyl-methoxy or completely or predominantly fluorine-substituted 1-2C-alkoxy,
R3 is hydrogen,
R31 is hydrogen,
R4 is hydrogen, 1-4C-alkyl, completely or predominantly fluorine-substituted 1-2C-alkyl, 1-2C-alkoxy-1-2C-alkyl, 2-hydroxyethyl or 1-7C-alkylcarbonyl,
R5 is hydrogen,
R6 is hydrogen, 1-4C-alkyl, 1-4C-alkoxy, completely or predominantly fluorine-substituted 1-2C-alkoxy, 3-7C-cycloalkoxy, 3-7C-cycloalkylmethoxy, halogen, nitro, amino, mono- or di-1-4C-alkylamino, 1-4C-alkylcarbonylamino or C(O)OR61, wherein
R61 is hydrogen, 1-4C-alkyl, 3-5C-cycloalkyl or 3-5C-cycloalkylmethyl,
R7 is hydrogen, 1-4C-alkyl, halogen, 1-4C-alkoxy, completely or predominantly fluorine-substituted 1-2C-alkoxy, 3-7C-cycloalkoxy or 3-7C-cycloalkylmethoxy, and the salts, the N-oxides and the salts of the N-oxides of these compounds.

Compounds of embodiment b, which are particularly to be emphasized, are those compounds of the formula I in which
R1 is 1-2C-alkoxy,
R2 is 1-2C-alkoxy,
R3 is hydrogen,
R31 is hydrogen,
R4 is hydrogen, 1-4C-alkyl, 1-2C-alkoxy-1-2C-alkyl or 1-7C-alkylcarbonyl,
R5 is hydrogen,
R6 is 1-4C-alkoxy, 3-7C-cycloalkylmethoxy, nitro, mono- or di-1-4C-alkylamino or C(O)OR61, where
R61 is hydrogen or 1-4C-alkyl,
R7 is hydrogen, 1-4C-alkoxy or 3-7C-cycloalkylmethoxy, and the salts, the N-oxides and the salts of the N-oxides of these compounds.

Preferred compounds of embodiment b are those compounds of the formula I in which
R1 is 1-2C-alkoxy,
R2 is 1-2C-alkoxy,
R3 is hydrogen,
R31 is hydrogen,
R4 is hydrogen or 1-4C-alkylcarbonyl,
R5 is hydrogen,
R6 is 1-4C-alkoxy, 3-7C-cycloalkylmethoxy, nitro, mono- or di-1-4C-alkylamino or C(O)OR61, wherein
R61 is hydrogen or 1-4C-alkyl,
R7 is hydrogen, 1-4C-alkoxy or 3-7C-cycloalkylmethoxy, and the salts, the N-oxides and the salts of the N-oxides of these compounds.

Particularly preferred compounds of embodiment b are those compounds of the formula I in which
R1 is methoxy,
R2 is methoxy,
R3 is hydrogen,
R31 is hydrogen,
R4 is hydrogen or acetyl,
R5 is hydrogen,
R6 is methoxy, cyclopropylmethoxy, nitro, dimethylamino or C(O)OR61, wherein R61 is hydrogen or methyl,
R7 is hydrogen, methoxy or cyclopropylmethoxy, and the salts, the N-oxides and the salts of the N-oxides of these compounds.

Preferred exemplary compounds of the formula I are (±)-acetic acid (2RS,4aRS,10bRS)-6-(3,4-bis-cyclopropylmethoxyphenyl)-8,9-dimethoxy-(1,2,3,4,4a,10b)-hexahydrophenanthridin-2-yl ester, (±)-acetic acid (2RS,4aRS,10bRS)-6-(4-methoxycarbonylphenyl)-8,9-dimethoxy-(1,2,3,4,4a,10b)-hexahydrophenanthridin-2-yl ester, (±)-acetic acid (2RS,4aRS,10bRS)-6-(4-dimethylaminophenyl)-8,9-dimethoxy-(1,2,3,4,4a,10b)-hexahydrophenanthridin-2-yl ester, (±)-acetic acid (2RS,4aRS,10bRS)-6-(3,4-dimethoxyphenyl)-8,9-dimethoxy-(1,2,3,4,4a,10b)-hexahydrophenanthridin-2-yl ester, (±)-acetic acid (2RS,4aRS,10bRS)-6-(4-nitrophenyl)-8,9-dimethoxy-(1,2,3,4,4a,10b)-hexahydrophenanthridin-2-yl ester, (±)-acetic acid (2SR,4aRS,10bRS)-6-(3,4-bis-cyclopropylmethoxyphenyl)-8,9-dimethoxy-(1,2,3,4,4a,10b)-hexahydrophenanthridin-2-yl ester, (±)-(2RS,4aRS,10bRS)-6-(3,4-bis-cyclopropylmethoxyphenyl)-8,9-dimethoxy-(1,2,3,4,4a,10b)-hexahydrophenanthridin-2-ol, (±)-(2RS,4aRS,10bRS)-6-(4-methoxycarbonylphenyl)-8,9-dimethoxy-(1,2,3,4,4a,10b)-hexahydrophenanthridin-2-ol, (±)-(2RS,4aRS,10bRS)-6-(4-dimethylaminophenyl)-8,9-dimethoxy-(1,2,3,4,4a,10b)-hexahydrophenanthridin-2-ol, (±)-(2RS,4aRS,10bRS)-6-(3,4-dimethoxyphenyl)-8,9-dimethoxy-(1,2,3,4,4a,10b)-hexahydrophenanthridin-2-ol, (±)-(2RS,4aRS,10bRS)-6-(4-nitrophenyl)-8,9-dimethoxy-(1,2,3,4,4a,10b)-hexahydrophenanthridin-2-ol, (±)-(2RS,4aRS,10bRS)-6-(4-carboxyphenyl)-8,9-dimethoxy-(1,2,3,4,4a,10b)-hexahydrophenanthridin-2-ol, (±)-(2SR,4aRS,10bRS)-6-(3,4-bis-cyclopropylmethoxyphenyl)-8,9-dimethoxy-(1,2,3,4,4a,10b)-hexahydrophenanthridin-2-ol, (±)-acetic acid (2RS,4aRS,10bRS)-6-(4-butoxy-phenyl)-8,9-dimethoxy-1,2,3,4,4a,10b-hexahydrophenanthridin-2-yl ester, (±)-acetic acid (2RS,4aRS,10bRS)-8,9-dim ethoxy-6-(4-methoxy-phenyl)-1,2,3,4,4a,10b-hexahydrophenanthridin-2-yl ester, (±)-acetic acid (2RS,4aRS,10bRS)-6-(4-cyano-phenyl)-8,9-dimethoxy-1,2,3,4,4a,10b-hexahydrophenanthridin-2-yl ester, (±)-acetic acid 4-((2RS,4aRS,10bRS)-2-acetoxy-8,9-dimethoxy-1,2,3,4,4a,10b-hexahydrophenanthridin-6-yl)-phenyl ester, (±)-acetic acid (2RS,4aRS,10bRS)-6-(4-acetylamino-phenyl)-8,9-dimethoxy-1,2,3,4,4a,10b-hexahydrophenanthridin-2-yl ester, (±)-acetic acid (2RS,4aRS,10bRS)-6-(4-chloro-phenyl)-8,9-dimethoxy-1,2,3,4,4a,10b-hexahydrophenanthridin-2-yl ester, (±)-acetic acid (2RS,4aRS,10bRS)-6-(2-chloro-phenyl)-8,9-dimethoxy-1,2,3,4,4a,10b-hexahydrophenanthridin-2-yl ester, (±)-acetic acid (2RS,4aRS,10bRS)-8,9-dimethoxy-6-(4-methoxy-3-propoxy-phenyl)-1,2,3,4,4a,10b-hexahydro-phenanthridin-2-yl ester,
(±)-acetic acid (2RS,4aRS,10bRS)-8,9-dimethoxy-6-p-tolyl-1,2,3,4,4a,10b-hexahydrophenanthridin-2-yl ester,
(±)-4-((2RS,4aRS,10bRS)-2-acetoxy-9-ethoxy-8-methoxy-1,2,3,4,4a,10b-hexahydrophenanthridin-6-yl)-benzoic acid methyl ester,
(±)-acetic acid (2RS,4aRS,10bRS)-9-ethoxy-6-(4-fluoro-phenyl)-8-methoxy-1,2,3,4,4a,10b-hexahydrophenanthridin-2-yl ester,
(±)-acetic acid (2RS,4aRS,10bRS)-6-(4-cyano-phenyl)-9-ethoxy-8-methoxy-1,2,3,4,4a,10b-hexahydrophenanthridin-2-yl ester,
(±)-acetic acid (2RS,4aRS,10bRS)-6-(3-cyclopropyl-methoxy-4-ethoxy-phenyl)-9-ethoxy-8-methoxy-1,2,3,4,4a,10b-hexahydrophenanthridin-2-yl ester,
(±)-acetic acid (2RS,4aRS,10bRS)-6-[3-cyclopropyl-methoxy-4-(1,1-difluoro-methoxy)-phenyl]-9-ethoxy-8-methoxy-1,2,3,4,4a,10b-hexahydro-phenanthridin-2-yl ester,
(±)-acetic acid (2RS,4aRS,10bRS)-6-[3,4-bis-(1,1-difluoro-methoxy)-phenyl]-9-ethoxy-8-methoxy-1,2,3,4,4a,10b-hexahydro-phenanthridin-2-yl ester,
(±)-acetic acid (2RS,4aRS,10bRS)-6-[3-(1,1-difluoro-methoxy)-phenyl]-9-ethoxy-8-methoxy-1,2,3,4,4a,10b-hexahydro-phenanthridin-2-yl ester,
(±)-acetic acid (2RS,4aRS,10bRS)-9-ethoxy-8-methoxy-6-[4-(1,1,2,2-tetrafluoro-ethoxy)-phenyl]-1,2,3,4,4a,10b-hexahydro-phenanthridin-2-yl ester,
(±)-acetic acid (2RS,4aRS,10bRS)-9-ethoxy-8-methoxy-6-(4-trifluoromethoxy-phenyl)-1,2,3,4,4a,10b-hexahydro-phenanthridin-2-yl ester,
(±)-acetic acid (2RS,4aRS,10bRS)-9-ethoxy-6-(3-fluoro-4-methoxy-phenyl)-8-methoxy-1,2,3,4,4a,10b-hexahydro-phenanthridin-2-yl ester,
(±)-acetic acid (2RS,4aRS,10bRS)-6-(3,4-difluoro-phenyl)-9-ethoxy-8-methoxy-1,2,3,4,4a,10b-hexahydrophenanthridin-2-yl ester,
(±)-acetic acid (2RS,4aRS,10bRS)-9-ethoxy-6-(3-fluoro-phenyl)-8-methoxy-1,2,3,4,4a,10b-hexahydrophenanthridin-2-yl ester,
(±)-acetic acid (2RS,4aRS,10bRS)-6-(4-bromo-phenyl)-9-ethoxy-8-methoxy-1,2,3,4,4a,10b-hexahydrophenanthridin-2-yl ester,
(±)-acetic acid (2RS,4aRS,10bRS)-6-[4-(1,1-difluoro-methoxy)-phenyl]-8,9-dim ethoxy-1,2,3,4,4a,10b-hexahydro-phenanthridin-2-yl ester,
(±)-acetic acid (2RS,4aRS,10bRS)-8,9-dimethoxy-6-(4-phenoxy-phenyl)-1,2,3,4,4a,10b-hexahydro-phenanthridin-2-yl ester,
(±)-acetic acid (2RS,4aRS,10bRS)-6-(4-fluoro-phenyl)-8,9-dimethoxy-1,2,3,4,4a,10b-hexahydro-phenanthridin-2-yl ester,
(±)-acetic acid (2RS,4aRS,10bRS)-6-[3,4-bis-(1,1-difluoro-methoxy)-phenyl]-8-(1,1-difluoro-methoxy)-9-methoxy-1,2,3,4,4a,10b-hexahydro-phenanthridin-2-yl ester,
(±)-acetic acid (2RS,4aRS,10bRS)-6-(4-cyano-phenyl)-8-(1,1-difluoro-methoxy)-9-methoxy-1,2,3,4,4a,10b-hexahydro-phenanthridin-2-yl ester,
(±)-4-[(2RS,4aRS,10bRS)-2-acetoxy-8-(1,1-difluoro-methoxy)-9-methoxy-1,2,3,4,4a,10b-hexahydro-phenanthridin-6-yl]-benzoic acid methyl ester,
(±)-4-[(2RS,4aRS,10bRS)-2-acetoxy-9-(1,1-difluoro-methoxy)-8-methoxy-1,2,3,4,4a,10b-hexahydro-phenanthridin-6-yl]-benzoic acid methyl ester, (±)-(2RS,4aRS,10bRS)-6-(4-butoxy-phenyl)-8,9-dimethoxy-1,2,3,4,4a,10b-hexahydro-phenanthridin-2-ol,
(±)-(2RS,4aRS,10bRS)-6-(4-fluoro-phenyl)-8,9-dimethoxy-1,2,3,4,4a,10b-hexahydro-phenanthridin-2-ol,
(±)-N-[4-((2RS,4aRS,10bRS)-2-hydroxy-8,9-dimethoxy-1,2,3,4,4a,10b-hexahydro-phenanthridin-6-yl)-phenyl]-acetamide,
(±)-(2RS,4aRS,10bRS)-6-(4-chloro-phenyl)-8,9-dimethoxy-1,2,3,4,4a,10b-hexahydro-phenanthridin-2-ol,
(±)-(2RS,4aRS,10bRS)-6-(2-chloro-phenyl)-8,9-dimethoxy-1,2,3,4,4a,10b-hexahydro-phenanthridin-2-ol,
(±)-(2RS,4aRS,10bRS)-8,9-dimethoxy-6-(4-methoxy-3-propoxy-phenyl)-1,2,3,4,4a,10b-hexahydro-phenanthridin-2-ol, (±)-(2RS, 4aRS,10bRS)-6-[4-(1,1-difluoro-methoxy)-phenyl]-8,9-dimethoxy-1,2,3,4,4a,10b-hexahydro-phenanthridin-2-ol,
(±)-4-((2RS,4aRS,10bRS)-9-ethoxy-2-hydroxy-8-methoxy-1,2,3,4,4a,10b-hexahydro-phenanthridin-6-yl)-benzoic acid methyl ester,
(±)-(2RS,4aRS,10bRS)-9-ethoxy-6-(4-fluoro-phenyl)-8-methoxy-1,2,3,4,4a,10b-hexahydro-phenanthridin-2-ol,
(±)-4-((2RS,4aRS,10bRS)-9-ethoxy-2-hydroxy-8-methoxy-1,2,3,4,4a,10b-hexahydro-phenanthridin-6-yl)-benzonitrile,
(±)-(2RS,4aRS,10bRS)-6-(3-cyclopropylmethoxy-4-ethoxy-phenyl)-9-ethoxy-8-methoxy-1,2,3,4,4a,10b-hexahydro-phenanthridin-2-ol,
(±)-(2RS,4aRS,10bRS)-6-[3-cyclopropylmethoxy-4-(1,1-difluoro-methoxy)-phenyl]-9-ethoxy-8-methoxy-1,2,3,4,4a,10b-hexahydro-phenanthridin-2-ol,
(±)-(2RS,4aRS,10bRS)-6-[3,4-bis-(1,1-difluoro-methoxy)-phenyl]-9-ethoxy-8-methoxy-1,2,3,4,4a,10b-hexahydro-phenanthridin-2-ol,
(±)-(2RS,4aRS,10bRS)-6-[3-(1,1-difluoro-methoxy)-phenyl]-9-ethoxy-8-methoxy-1,2,3,4,4a,10b-hexahydro-phenanthridin-2-ol,
(±)-(2RS,4aRS,10bRS)-9-ethoxy-8-methoxy-6-[4-(1,1,2,2-tetrafluoro-ethoxy)-phenyl]-1,2,3,4,4a,10b-hexahydro-phenanthridin-2-ol,
(±)-(2RS,4aRS,10bRS)-9-ethoxy-8-methoxy-6-(4-trifluoromethoxy-phenyl)-1,2,3,4,4a,10b-hexahydro-phenanthridin-2-ol,
(±)-(2RS,4aRS,10bRS)-9-ethoxy-6-(3-fluoro-4-methoxy-phenyl)-8-methoxy-1,2,3,4,4a,10b-hexahydro-phenanthridin-2-ol,
(±)-(2RS,4aRS,10bRS)-6-(3,4-difluoro-phenyl)-9-ethoxy-8-methoxy-1,2,3,4,4a,10b-hexahydro-phenanthridin-2-ol,
(±)-(2RS,4aRS,10bRS)-9-ethoxy-6-(3-fluoro-phenyl)-8-methoxy-1,2,3,4,4a,10b-hexahydro-phenanthridin-2-ol,
(±)-(2RS,4aRS,10bRS)-6-(4-bromo-phenyl)-9-ethoxy-8-methoxy-1,2,3,4,4a,10b-hexahydro-phenanthridin-2-ol,
(±)-(2RS,4aRS,10bRS)-8,9-dimethoxy-6-p-tolyl-1,2,3,4,4a,10b-hexahydro-phenanthridin-2-ol,
(±)-(2RS,4aRS,10bRS)-8,9-dimethoxy-6-(4-phenoxy-phenyl)-1,2,3,4,4a,10b-hexahydro-phenanthridin-2-ol,
(±)-(2RS,4aRS,10bRS)-8,9-dimethoxy-6-(4-methoxy-phenyl)-1,2,3,4,4a,10b-hexahydrophenanthridin-2-ol,
(±)-4-((2RS,4aRS,10bRS)-2-hydroxy-8,9-dimethoxy-1,2,3,4,4a,10b-hexahydro-phenanthridin-6-yl)-benzonitrile,
(±)-(2RS,4aRS,10bRS)-6-[3,4-bis-(1,1-difluoro-methoxy)-phenyl]-8-(1,1-difluoro-methoxy)-9-methoxy-1,2,3,4,4a,10b-hexahydro-phenanthridin-2-ol,
(±)-4-[(2RS,4aRS,10bRS)-8-(1,1-difluoro-methoxy)-2-hydroxy-9-methoxy-1,2,3,4,4a,10b-hexahydro-phenanthridin-6-yl]-benzonitrile, (±)-4-[(2RS,4aRS,10bRS)-8-(1,1-difluoro-methoxy)-2-hydroxy-9-methoxy-1,2,3,4,4a,10b-hexahydro-phenanthridin-6-yl]-benzoic acid methyl ester, (±)-4-[(2RS,4aRS,10bRS)-9-(1,1-difluoro-methoxy)-2-hydroxy-8-methoxy-1,2,3,4,4a,10b-hexahydro-phenanthridin-6-yl]-benzoic acid methyl ester, (±)-acetic acid (2RS,4aRS,10bRS)-6-(4-hydroxy-phenyl)-8,9-dimethoxy-1,2,3,4,4a,10b-hexahydro-phenanthridin-2-yl ester, (±)-4-((2RS,4aRS,10bRS)-2-acetoxy-8,9-dimethoxy-1,2,3,4,4a,10b-hexahydro-phenanthridin-6-yl)-benzoic acid hydrochloride, (±)-4-((2RS,4aRS,10bRS)-2-acetoxy-9-(1,1-difluoro-methoxy)-8-methoxy-1,2,3,4,4a,10b-hexahydro-phenanthridin-6-yl)-benzoic acid, (±)-(2RS,4aRS,10bRS)-6-(3,4-bis-cyclopropylmethoxy-phenyl)-2,8,9-trimethoxy-1,2,3,4,4a,10b-hexahydro-phenanthridine, (±)-(2RS,4aRS,10bRS)-6-(3,4-bis-cyclopropylmethoxy-phenyl)-2-ethoxy-8,9-dimethoxy-1,2,3,4,4a,10b-hexahydro-phenanthridine, and (±)-(2RS,4aRS, 10bRS)-6-(3,4-bis-cyclopropylmethoxy-phenyl)-8,9-dimethoxy-2-(2-methoxy-ethoxy)-1,2,3,4,4a,10b-hexahydro-phenanthridine, and the salts, the N-oxides and the salts of the N-oxides of these compounds.

A special embodiment of the compounds of the present invention include those compounds of the formula I in which R1 and R2 are 1-2C-alkoxy.

A further special embodiment of the compounds of the present invention include those compounds of the formula I in which R1 and R2 are 1-2C-alkoxy and R3, R31 and R5 are hydrogen.

Another further special embodiment of the compounds of the present invention include those compounds of the formula I in which R4 is hydrogen.

Also another further special embodiment of the compounds of the present invention include those compounds of the formula I in which R6 is 1-4C-alkoxy, completely or predominantly fluorine-substituted 1-4C-alkoxy, 3-7C-cycloalkylmethoxy, halogen, nitro, cyano, phenoxy or C(O)OR61, wherein R61 is hydrogen or 1-7C-alkyl, and R7 is hydrogen, halogen, 1-4C-alkoxy, completely or predominantly fluorine-substituted 1-4C-alkoxy, or 3-7C-cycloalkylmethoxy.

A still further special embodiment of the compounds of the present invention include those compounds of the formula I in which R1 is 1-2C-alkoxy, or completely or predominantly fluorine-substituted 1-2C-alkoxy, R2 is 1-2C-alkoxy, or completely or predominantly fluorine-substituted 1-2C-alkoxy, and R3, R31 and R5 are hydrogen, whereby in this context compounds to be emphasized include those compounds of the formula I in which R1 is ethoxy, and
R2 is methoxy or difluoromethoxy;
or, in particular,
R1 is methoxy or difluoromethoxy, and
R2 is methoxy, difluoromethoxy or ethoxy;
or, in more particular,
either
R1 is difluoromethoxy, and
R2 is methoxy or ethoxy,
or
R1 is methoxy, and
R2 is ethoxy or difluoromethoxy;
and R3, R31 and R5 are hydrogen.

The compounds of the formula I are chiral compounds having chiral centers at least in positions 2, 4a and 10b and, depending on the meaning of the substituents R3, R31 and R5, further chiral centers in the positions 1, 3 and 4.

Numbering:

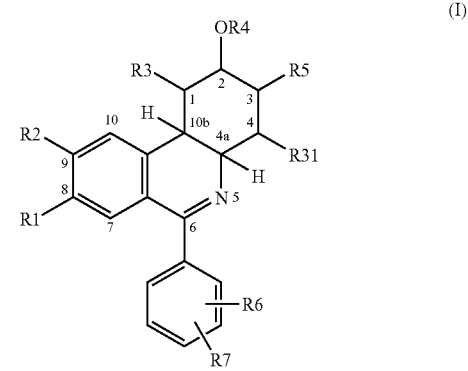

(I)

The invention therefore comprises all conceivable stereoisomers in pure form as well as in any mixing ratio.

Preferred compounds of the formula I are those in which the hydrogen atoms in positions 4a and 10b are in the cis position relative to one another. The pure cis diastereomers, the pure cis enantiomers and their mixtures in any mixing ratio and including the racemates are more preferred in this context. Particularly preferred in this connection are those compounds of the formula I which have, with respect to the positions 4a and 10b, the same configuration as shown in the formula I*:

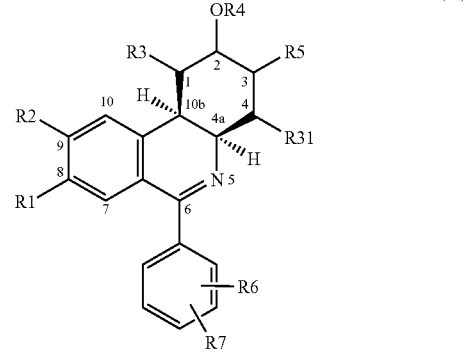

(I*)

If, for example in compounds of the formula I* R3, R31 and R5 have the meaning hydrogen, then the configuration—according the rules of Cahn, Ingold and Prelog—is R in the position 4a and R in the position 10b.

Further preferred compounds of the formula I are those which have, with respect to the positions 2, 4a and 10b, the same configuration as shown in the formulae I and I* and I****:

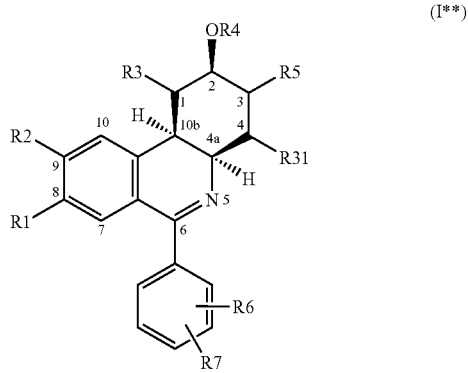

(I**)

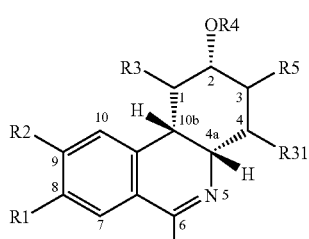

(I***)

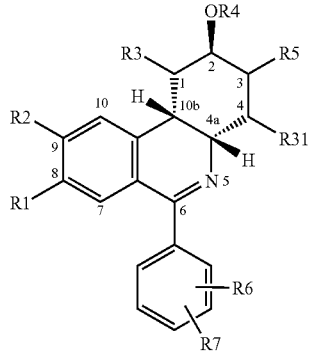

(I****)

If, for example in compounds of the formula I** R3, R31 and R5 have the meaning hydrogen, then the configuration—according the rules of Cahn, Ingold and Prelog—is S in the position 2, R in the position 4a and R in the position 10b.

If, for example in compounds of the formula I*** R3, R31 and R5 have the meaning hydrogen, then the configuration—according the rules of Cahn, Ingold and Prelog—is R in the position 2, S in the position 4a and S in the position 10b.

If, for example in compounds of the formula I**** R3, R31 and R5 have the meaning hydrogen, then the configuration—according the rules of Cahn, Ingold and Prelog—is S in the position 2, S in the position 4a and S in the position 10b.

Most preferred compounds of the formula I are those which have, with respect to the positions 2, 4a and 10b, the same configuration as shown in the formula I*****:

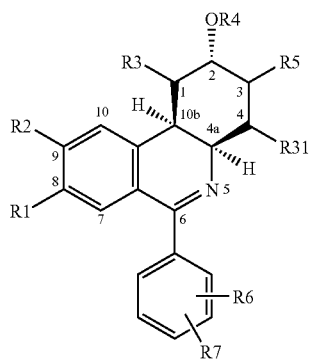

(I*****)

If, for example in compounds of the formula I***** R3, R31 and R5 have the meaning hydrogen, then the configuration—according the rules of Cahn, Ingold and Prelog—is R in the position 2, R in the position 4a and R in the position 10b.

As stated above all other possible stereoisomers of compounds of the formula I are also part of this invention.

The enantiomers can be separated in a manner known per se (for example by preparation and separation of appropriate diastereoisomeric compounds). For example, an enantiomer separation can be carried out at the stage of the starting compounds of the formula IVa, in which R1, R2, R3, R31 and R5 have the meanings indicated above and PG represents a suitable protecting group, for example acetyl. Further suitable protecting groups are mentioned, for example, in "Protective Groups in Organic Synthesis" by T. Greene and P. Wuts (John Wiley & Sons, Inc. 1999, $3^{rd}$ Ed.) or in "Protecting Groups (Thieme Foundations Organic Chemistry Series N Group" by P. Kocienski (Thieme Medical Publishers, 2000). Alternatively, an enantiomer separation can be also carried out at the stage of the starting compounds of the formula IVb, in which R1, R2, R3, R31, R4 and R5 have the meanings indicated above.

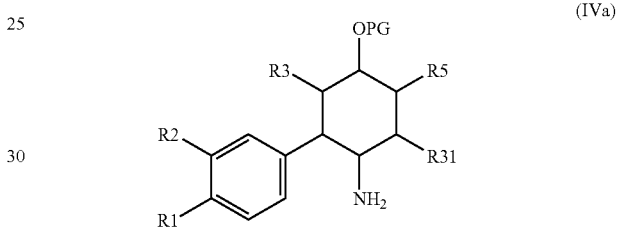

(IVa)

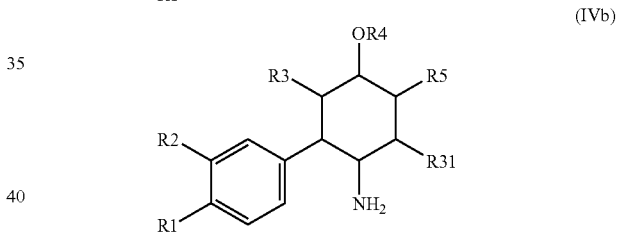

(IVb)

Separation of the enantiomers can be carried out, for example, by means of salt formation of the racemic compounds of the formulae IVa or IVb with optically active carboxylic acids, subsequent resolution of the salts and release of the desired compound from the salt. Examples of optically active carboxylic acids which may be mentioned in this connection are the enantiomeric forms of mandelic acid, tartaric acid, O,O'-dibenzoyltartaric acid, camphoric acid, quinic acid, glutamic acid, malic acid, camphorsulfonic acid, 3-bromocamphorsulfonic acid, α-methoxyphenylacetic acid, α-methoxy-α-trifluoromethylphenylacetic acid and 2-phenylpropionic acid. Alternatively, enantiomerically pure starting compounds of the formulae IVa or IVb can be prepared via asymmetric syntheses. Enantiomerically pure starting compounds as well as enantiomerically pure compounds of the formula I can be also obtained by chromatographic separation on chiral separating columns; by derivatization with chiral auxiliary reagents, subsequent diastereomer separation and removal of the chiral auxiliary group; or by (fractional) crystallization from a suitable solvent.

The compounds according to the invention can be prepared, for example, as shown in the following reaction schemes.

Reaction scheme 1:
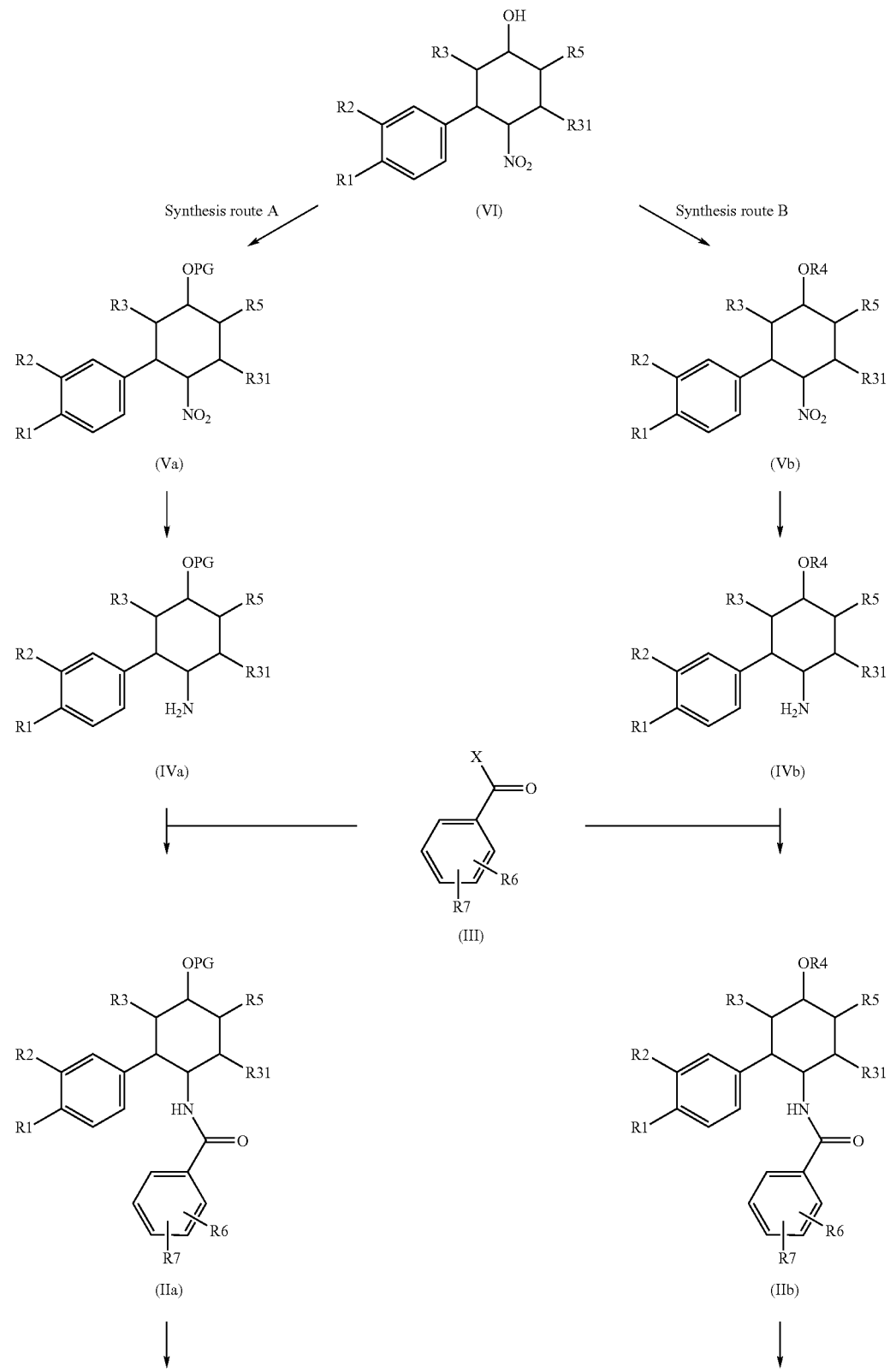

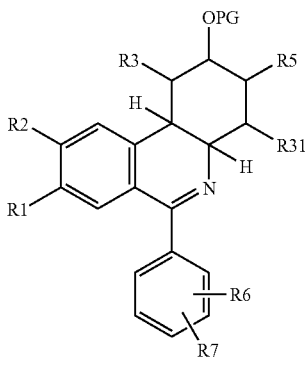

(Ia)

-continued

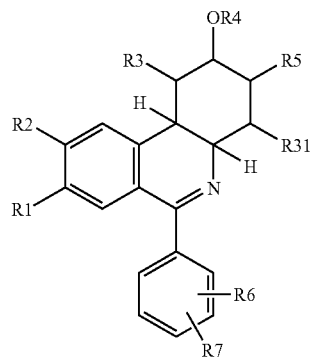

(I)

According to reaction scheme 1 above, compounds of the formula I can be obtained via different routes. On the one hand compounds of the formula I can be accessible via synthesis route A, which is outlined in the left column of reaction scheme 1, using a temporary protective group to protect the hydroxyl group. On the other hand compounds of the formula I can be also obtained via synthesis route B, which is outlined in the right column of reaction scheme 1, by introducing the group R4 already in the initial step of synthesis route B.

Abovementioned synthesis route A comprise the subsequently specified reaction steps: In the first reaction step, the free hydroxyl group of compounds of the formula VI, wherein R1, R2, R3, R31 and R5 have the meanings indicated above, is protected by a suitable protective group, for example acetyl or one of those mentioned in "Protective Groups in Organic Synthesis" by T. Greene and P. Wuts (John Wiley & Sons, Inc. 1999, $3^{rd}$ Ed.) or in "Protecting Groups (Thieme Foundations Organic Chemistry Series N Group" by P. Kocienski (Thieme Medical Publishers, 2000). Said protection reaction is carried out in a manner familiar to the person skilled in the art or as described in the following examples to obtain compounds of the formula Va, in which R1, R2, R3, R31 and R5 have the meanings mentioned above and PG represents said suitable protective group.

In the next reaction step of synthesis route A, the nitro group of compounds of the formula Va, in which R1, R2, R3, R31 and R5 have the abovementioned meanings and PG represents said suitable protective group, is reduced to the amino group of the corresponding compounds of the formula IVa. The said reduction is carried out in a manner known to the person skilled in the art, for example as described in J. Org. Chem. 1962, 27, 4426 or as described in the following examples. In more detail, the reduction can be carried out, for example, by catalytic hydrogenation, e.g. in the presence of Raney nickel or a noble metal catalyst such as palladium on active carbon, in a suitable solvent such as methanol or ethanol at room temperature and under normal or elevated pressure. Optionally, a catalytic amount of an acid, such as, for example, hydrochloric acid, can be added to the solvent. Preferably, however, the reduction is carried out using a hydrogen-producing mixture, for example, metals such as zinc, zinc-copper couple or iron with organic acids such as acetic acid or mineral acids such as hydrochloric acid. Most preferably, the reduction is carried out using a zinc-copper couple in the presence of an organic or an inorganic acid. Such a zinc-copper couple is accessible in a way known to the person of ordinary skill in the art. Compounds of the formula IVa, in which R1, R2, R3, R31, R5 and PG have the meanings indicated above and which are sensitive against catalytic hydrogenation, can be prepared from the corresponding compounds of the formula Va by selective reduction of the nitro group in a manner known to the person skilled in the art, for example by hydrogen transfer reaction in the presence of a metal catalyst, for example palladium or, preferably, Raney nickel, in a lower alcohol as solvent using, for example, ammonium formiate or, preferably, hydrazine hydrate as hydrogen donor.

Compounds of the formula IIa, in which R1, R2, R3, R31, R5, R6 and R7 have the meanings indicated above and PG represents said protective group, are accessible from the corresponding compounds of the formula IVa, for example, as described in the following examples by reaction with compounds of the formula III, in which R6 and R7 have the meanings given above and X represents a suitable leaving group, preferably a chlorine atom.

Alternatively, compounds of the formula IIa, in which R1, R2, R3, R31, R5, R6 and R7 have the meanings indicated above and PG represents said protective group, can also be prepared, for example, as described in the following examples from the corresponding compounds of the formula IVa and compounds of the formula III, in which R6 and R7 have the said meanings and X is hydroxyl, by reaction with amide bond linking reagents known to the person skilled in the art. Exemplary amide bond linking reagents known to the person skilled in the art which may be mentioned are, for example, the carbodiimides (e.g. dicyclohexylcarbodiimide or, preferably, 1-ethyl-3-(3-dimethylaminopropyl)carbodiimide hydrochloride), azodicarboxylic acid derivatives (e.g. diethyl azodicarboxylate), uronium salts [e.g. O-(benzotriazol-1-yl)-N,N,N',N'-tetramethyluronium tetrafluoroborate or O-(benzotriazol-1-yl)-N,N,N',N'-tetramethyl-uronium-hexafluorophosphate] and N,N'-carbonyldiimidazole. In the scope of this invention preferred amide bond linking reagents are uronium salts and, particularly, carbodiimides, preferably, 1-ethyl-3-(3-dimethylaminopropyl)carbodiimide hydrochloride.

Compounds of the formula III are either known or can be prepared in a known manner.

Compounds of the formula Ia, in which R1, R2, R3, R31, R5, R6 and R7 have the meanings indicated above and PG represents said suitable protective group, are obtained by cyclocondensation of corresponding compounds of the formula IIa.

Said cyclocondensation reaction is carried out in a manner known per se to the person skilled in the art or as described by way of example in the following examples, according to Bischler-Napieralski (e.g. as described in J. Chem. Soc., 1956, 4280-4282) in the presence of a suitable condensing agent, such as, for example, polyphosphoric acid, phosphorus pentachloride, phosphorus pentoxide or phosphorus oxychloride, in a suitable inert solvent, e.g. in a chlorinated hydrocarbon such as chloroform, or in a cyclic hydrocarbon such as toluene or xylene, or another inert solvent such as isopropyl acetate or acetonitrile, or without further solvent using an excess of condensing agent, at reduced temperature, or at room temperature, or at elevated temperature or at the boiling temperature of the solvent or condensing agent used.

Compounds of the formula I, in which R1, R2, R3, R31, R4, R5, R6 and R7 have the meanings mentioned above, are accessible from compounds of the formula Ia, in which R1, R2, R3, R31, R5, R6 and R7 have the said meanings and PG represents said suitable protective group by reactions known to one of ordinary skill in the art or by reactions described, for example, in the following examples.

In more detail, for example, compounds of the formula I, in which R1, R2, R3, R31, R5, R6 and R7 have the meanings mentioned above and R4 is hydrogen, can be obtained from compounds of the formula Ia, in which R1, R2, R3, R31, R5, R6 and R7 have the abovementioned meanings and PG represents said suitable protective group, by removal of the protective group in a manner described in the following examples or according to an art-known manner mentioned, for example, in "Protective Groups in Organic Synthesis" by T. Greene and P. Wuts (John Wiley & Sons, Inc. 1999, 3$^{rd}$ Ed.) or in "Protecting Groups (Thieme Foundations Organic Chemistry Series N Group" by P. Kocienski (Thieme Medical Publishers, 2000).

Optionally, said compounds of the formula I, in which R1, R2, R3, R31, R5, R6 and R7 have the meanings mentioned above and R4 is hydrogen, can be further derivatisized, preferably at the free hydroxyl group in position 2, by suitable reactions known to the person skilled in the art to obtain further compounds of the formula I.

As stated above, compounds of the formula I, in which R1, R2, R3, R31, R4, R5, R6 and R7 have the meanings given above, can be also obtained according to the reaction scheme 1 via an alternative synthesis route, which is outlined in the right column of reaction scheme 1 and denoted as synthesis route B.

In the first reaction step of synthesis route B, compounds of the formula Vb, in which R1, R2, R3, R31, R4 and R5 have the meanings mentioned above, are prepared from the corresponding compounds of the formula VI by introduction of the group R4. The introduction reaction is carried out in a manner habitual per se or as described by way of example in the following examples.

The following reaction steps of synthesis route B lead successively to compounds of the formula IVb, compounds of the formula IIb and, finally, compounds of the formula I. Said reaction steps can be carried out as described by way of example in the following examples or according to known analogous or similar processes, such as, for example, the processes shown and already specified in synthesis route A.

Optionally, compounds of the formula I obtained either via synthesis route A or via synthesis route B can be also converted into further compounds of the formula I by methods known to one of ordinary skill in the art. More specifically, for example, from compounds of the formula I in which a) R6 and/or R7 are an ester group, the corresponding acids can be obtained by acidic or alkaline hydrolysis;
b) R6 is a 1-4C-alkylcarbonyloxy group, the corresponding hydroxyl compounds can be obtained by acidic or alkaline hydrolysis;
c) R6 is a nitro group, the corresponding amino compounds, which, for their part, can again be further derivatized, can be obtained by selective reduction of the nitro group;
d) R4 is hydrogen, the corresponding ester compounds can be obtained by esterification reactions;
e) R4 is hydrogen, the corresponding ether compounds can be obtained by etherification reactions;
f) R4 is an acyl group, the corresponding hydroxyl compounds can be obtained by deesterification reactions;
g) R4 is an acyl group and R6 and/or R7 are an ester group, the corresponding compounds wherein R4 is hydrogen and R6 and/or R7 are carboxyl can be obtained by alkaline hydrolysis.

The methods mentioned under a), b), c), d), e), f) and g) are expediently carried out analogously to the methods known to the person skilled in the art or as described by way of example in the following examples.

Optionally, compounds of the formula I can be converted into their salts, or, optionally, salts of the compounds of the formula I can be converted into the free compounds.

In addition, the compounds of the formula I can be converted, optionally, into their N-oxides, for example with the aid of hydrogen peroxide in methanol or with the aid of m-chloroperoxybenzoic acid in dichloromethane. The person skilled in the art is familiar on the basis of his/her expert knowledge with the reaction conditions which are specifically necessary for carrying out the N-oxidation.

Below reaction scheme 2 shows the synthesis of compounds of the formula VI, in which R1, R2, R3, R31 and R5 have the meanings indicated above, from corresponding compounds of the formula VIII via reduction reaction of the carbonyl group. Suitable reducing agents for the abovementioned reduction reaction may include, for example, metal hydride compounds such as, for example, diisopropylaluminum hydride, borane, sodium borohydride, sodium triacetoxyborohydride, sodium cyanoborohydride, zinc borohydride, potassium tri-sec-butylborohydride, sodium tri-sec-butylborohydride, lithium tri-sec-butylborohydride, β-isopinocampheyl-9-borabicyclo[3.3.1]nonane and the like. The preferred examples of said reducing agents are sodium cyanoborohydride, β-isopinocampheyl-9-borabicyclo[3.3.1]nonane and potassium tri-sec-butylborohydride. The most preferred examples of the abovementioned reducing agents are β-isopinocampheyl-9-borabicyclo[3.3.1]nonane and potassium tri-sec-butylborohydride, which both allow to prepare compounds of the formula VI stereoselectively. "Stereoselectively" in this connection means that those compounds of the formula VI, in which the hydrogen atoms in positions 1 and 3 are located at the opposite side of the plane defined by the cyclohexane ring, are obtained preferentially.

Reaction scheme 2:

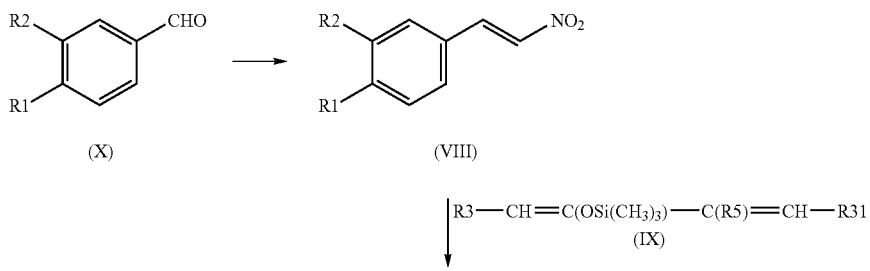

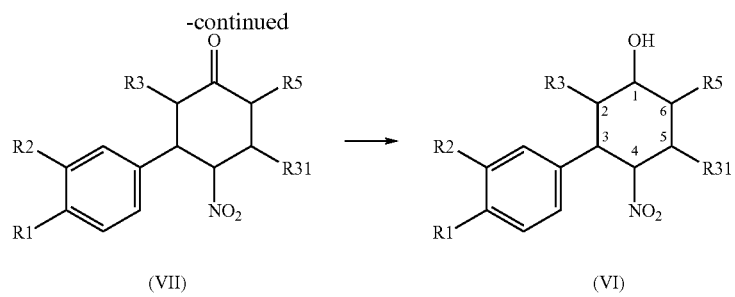

The compounds of the formula VII, in which R1, R2, R3, R31 and R5 have the said meanings, are either known or can be obtained by the reaction of compounds of the formula VIII, in which R1 and R2 have the meanings mentioned above, with compounds of the formula IX, in which R3, R31 and R5 have the meanings mentioned above. The cycloaddition reaction is carried out in a manner known to the person skilled in the art according to Diels-Alder, e.g. as described in J. Amer. Chem. Soc. 1957, 79, 6559 or in J. Org. Chem. 1952, 17, 581 or as described in the following examples.

Compounds of the formulae Va, Vb and VI, in which the phenyl ring and the nitro group are trans to one another, can be converted in a manner known to the person skilled in the art into the corresponding cis compounds, e.g. as described in J. Amer. Chem. Soc. 1957, 79, 6559 or as described in the following examples.

The compounds of the formulae VIII and IX are either known or can be prepared in a known manner. The compounds of the formula VIII can be prepared, for example, in a manner known to the person skilled in the art from corresponding compounds of the formula X as described, for example, in J. Chem. Soc. 1951, 2524 or in J. Org. Chem. 1944, 9, 170 or as described in the following examples.

The compounds of the formula X, in which R1 and R2 have the meanings indicated above, are either known or can be prepared in a manner known to the person skilled in the art, as described, for example, in Ber. Dtsch. Chem. Ges. 1925, 58, 203.

It is moreover known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in "Protective Groups in Organic Synthesis" by T. Greene and P. Wuts (John Wiley & Sons, Inc. 1999, 3$^{rd}$ Ed.) or in "Protecting Groups (Thieme Foundations Organic Chemistry Series N Group" by P. Kocienski (Thieme Medical Publishers, 2000).

The isolation and purification of the substances according to the invention is carried out in a manner known per se, e.g. by distilling off the solvent in vacuo and recrystallizing the resulting residue from a suitable solvent or subjecting it to one of the customary purification methods, such as, for example, column chromatography on suitable support material.

Salts are obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low molecular weight aliphatic alcohol such as ethanol or isopropanol) which contains the desired acid or base, or to which the desired acid or base is then added. The salts are obtained by filtering, reprecipitating, precipitating with a nonsolvent for the addition salt or by evaporating the solvent. Salts obtained can be converted by alkalization or by acidification into the free compounds, which in turn can be converted into salts. In this way, pharmacologically intolerable salts can be converted into pharmacologically tolerable salts.

The person skilled in the art knows on the basis of his/her knowledge and on the basis of those synthesis routes, which are shown and described within the description of this invention, how to find other possible synthesis routes for compounds of the formula I. All these other possible synthesis routes are also part of this invention.

Having described the invention in detail, the scope of the present invention is not limited only to those described characteristics or embodiments. As will be apparent to persons skilled in the art, modifications, analogies, variations and adaptations to the described invention can be made on the base of the disclosure (e.g. the explicite, implicite or inherent disclosure) of the present invention without departing from the spirit and scope of this invention.

The following examples serve to illustrate the invention further without restricting it. Likewise, further compounds of the formula I, whose preparation is not explicitly described, can be prepared in an analogous manner or in a manner familiar per se to the person skilled in the art using customary process techniques.

In the examples, m.p. stands for melting point, h for hour(s), min for minutes, $R_f$ for retention factor in thin layer chromatography, s.p. for sintering point, EF for empirical formula, MW for molecular weight, MS for mass spectrum, M for molecular ion.

According to common practice in stereochemistry, the symbols RS and SR are used to denote the specific configuration of each of the chiral centers of a racemate. In more detail, for example, the term "(2RS,4aRS,10bRS)" stands for a racemate comprising the one enantiomer having the configuration (2R,4aR,10bR) and the other enantiomer having the configuration (2S,4aS,10bS).

The compounds mentioned in the examples and their salts are a preferred subject of the invention.

EXAMPLES

Final Products 1. (±)-Acetic acid (2RS,4aRS,10bRS)-6-(3,4-bis-cyclopropylmethoxyphenyl)-8,9-dimethoxy-(1,2,3,4,4a,10 b)-hexahydrophenanthridin-2-yl ester 320 mg of (±)-acetic acid (1RS,3RS,4RS)-4-{[1-(3,4-bis-cyclopropylmethoxyphenyl)-methanoyl]-amino}-3-(3,4- dimethoxy-phenyl)-cyclohexyl ester (compound A1) in 3 ml of isopropyl acetate is added at 0° C. under nitrogen atmosphere to a suspension of 365 mg of phosphorus pentachloride in 2 ml of isopropyl acetate. The mixture is stirred for 50 min. Then a solution of 3.5 ml of triethylamine in 10 ml of isopropyl acetate is added dropwise. After diluting with 10 ml of water and 20 ml of isopropyl acetate, the phases are separated and the aqueous layer is extracted three times with isopropyl acetate. After concentrating, the residue is chromatographed on silica gel and 267 mg (86% of theory) of the title compound are obtained as a colourless foam.

EF: $C_{31}H_{37}NO_6$; MW: 519.64
MS: 520.2 (MH$^+$)
$R_f$=0.56 (petroleum ether/ethyl acetate/triethylamine=6/3/1)
M.p.: 73-77° C.

Starting from the starting compounds described below, the following are obtained according to the procedure as in Example 1:

2. (±)-Acetic acid (2RS,4aRS,10bRS)-6-(4-methoxycarbonylphenyl)-8,9-dimethoxy-(1,2,3,4,4a,10b)-hexahydrophenanthridin-2-yl ester EF: $C_{25}H_{27}NO_6$; MW: 437.50
MS: 438.3 (MH$^+$)
$R_f$=0.62 (petroleum ether/ethyl acetate/triethylamine=6/3/1)
M.p.: 184-185° C.

3. (±)-Acetic acid (2RS,4aRS,10bRS)-6-(4-dimethylaminophenyl)-8,9-dimethoxy-(1,2,3,4,4a,10b)-hexahydrophenanthridin-2-yl ester EF: $C_{25}H_{30}N_2O_4$; MW: 422.53
MS: 423.3 (MH$^+$)
$R_f$=0.52 (petroleum ether/ethyl acetate/triethylamine=4/5/1)

4. (±)-Acetic acid (2RS,4aRS,10bRS)-6-(3,4-dimethoxyphenyl)-8,9-dimethoxy-(1,2,3,4,4a,10b)-hexahydrophenanthridin-2-yl ester EF: $C_{25}H_{29}NO_6$; MW: 439.51
MS: 440.3 (MH$^+$)
$R_f$=0.35 (petroleum ether/ethyl acetate/triethylamine=5/4/1)
M.p.: 86-94° C.

5. (±)-Acetic acid (2RS,4aRS,10bRS)-6-(4-nitrophenyl)-8,9-dimethoxy-(1,2,3,4,4a,10b)-hexahydrophenanthridin-2-yl ester EF: $C_{24}H_{23}N_2O_6$; MW: 424.46
MS: 425.3 (MH$^+$)
$R_f$=0.41 (petroleum ether/ethyl acetate/triethylamine=6/3/1)
M.p.: 77-88° C.

6. (±)-Acetic acid (2SR,4aRS,10bRS)-6-(3,4-bis-cyclopropylmethoxyphenyl)-8,9-dimethoxy-(1,2,3,4,4a,10b)-hexahydrophenanthridin-2-yl ester 670 mg of (±)-acetic acid (1SR,3RS,4RS)-4-{[1-(3,4-bis-cyclopropylmethoxyphenyl)-methanoyl]-amino}-3-(3,4-dimethoxy-phenyl)-cyclohexyl ester (compound A6) are added portionwise to a suspension of 1.0 g of phosphorus pentachloride in 10 ml of isopropyl acetate. After 1 h the reaction mixture is dropped to an ice cooled solution of 7 ml of triethylamine in 20 ml of isopropyl acetate. After diluting with 20 ml of water, the mixture is washed with saturated sodium hydrogencarbonate solution, the phases are separated and the organic phase is dried using sodium sulfate and concentrated. The residue is chromatographed on silica gel using a mixture of petroleum ether/ethyl acetate/triethylamine in the ratio 6/3/1. After concentration of the corresponding eluate fractions, 520 mg of the title compound are obtained as a slight yellow oil.

7. (±)-(2RS,4aRS,10bRS)-6-(3,4-Bis-cyclopropyl-methoxyphenyl)-8,9-dimethoxy-(1,2,3,4,4a,10b)-hexahydrophenanthridin-2-ol Under nitrogen 200 mg of (±)-acetic acid (2RS,4aRS,10bRS)-6-(3,4-bis-cyclopropylmethoxyphenyl)-8,9-dimethoxy-(1,2,3,4,4a,10b)-hexahydrophenanthridin-2-yl ester (compound 1) are dissolved in 5 ml of methanol, treated with 32 mg of cesium carbonate and the mixture is stirred for 15 min at room temperature. After 15 min further 32 mg of cesium carbonate are added and stirring is continued for 15 h. The reaction mixture is adsorbed on silica gel and chromatographed and 170 mg (92% of theory) of the title compound are obtained as a slight yellow solid.

EF: $C_{29}H_{35}NO_5$; MW: 477.61
MS: 478.3 (MH$^+$)
$R_f$=0.56 (ethyl acetate/triethylamine=9/1)
M.p.: 83-92° C.

Starting from the starting compounds described above in Example 2 to 5, the following are obtained according to the procedure as in Example 7:

8. (±)-(2RS,4aRS,10bRS)-6-(4-Methoxycarbonylphenyl)-8,9-dimethoxy-(1,2,3,4,4a,10b)-hexahydrophenanthridin-2-ol EF: $C_{23}H_{25}NO_5$; MW: 395.46
MS: 396.4 (MH$^+$)
$R_f$=0.35 (ethyl acetate/triethylamine=9/1)
M.p.: 94-105° C.

9. (±)-(2RS,4aRS,10bRS)-6-(4-Dimethylaminophenyl)-8,9-dimethoxy-(1,2,3,4,4a,10b)-hexahydrophenanthridin-2-ol EF: $C_{23}H_{28}N_2O_3$; MW: 380.49
MS: 381.4 (MH$^+$)
$R_f$=0.36 (ethyl acetate/triethylamine=9/1)
M.p.: 115-121° C.

10. (±)-(2RS,4aRS,10bRS)-6-(3,4-Dimethoxyphenyl)-8,9-dimethoxy-(1,2,3,4,4a,10b)-hexahydrophenanthridin-2-ol EF: $C_{23}H_{27}NO_5$; MW: 397.48
MS: 398.4 (MH$^+$)
$R_f$=0.30 (ethyl acetate/triethylamine=9/1)
M.p.: 104-110° C.

11. (±)-(2RS,4aRS, 10bRS)-6-(4-Nitrophenyl)-8,9-dimethoxy-(1,2,3,4,4a,10b)-hexahydrophenanthridin-2-ol EF: $C_{21}H_{22}N_2O_5$; MW: 382.42
MS: 383.3 (MH$^+$)
$R_f$=0.57 (ethyl acetate/triethylamine=9/1)
M.p.: 178-181° C.

12. (±)-(2RS,4aRS,10bRS)-6-(4-Carboxyphenyl)-8,9-dimethoxy-(1,2,3,4,4a,10b)-hexahydro-phenanthridin-2-ol A solution of 290 mg (0.66 mmol) of (±)-acetic acid (2RS,4aRS,10bRS)-6-(4-methoxycarbonylphenyl)-8,9-dimethoxy-(1,2,3,4,4a,10b)-hexahydrophenanthridin-2-yl ester (compound 2) in 10 ml of isopropanol is treated dropwise with aqueous lithium hydroxide solution to adjust to pH 10. Stirring is continued for 72 h, the reaction mixture is neutralized with phosphate buffer solution and extracted with dichloromethane. The aqueous layer is concentrated and the residue is leached with a boiling mixture of ethyl acetate and methanol. The organic solvents are removed to obtain 90 mg of the title compound as a yellowish foam.

EF: $C_{22}H_{23}NO_5$; MW: 381.43
MS: 382.4 (MH$^+$)
M.p.: 172-183° C.

Alternative procedure:

A solution of 5.68 g of (±)-acetic acid (2RS,4aRS,10bRS)-6-(4-methoxycarbonylphenyl)-8,9-dimethoxy-(1,2,3,4,4a,10b)-hexahydrophenanthridin-2-yl ester (compound 2) in 250 ml of methanol is treated at boiling temperature with a solution of 2.0 g of sodium hydroxide in 15 ml of water comprising a catalytic amount of hydrogen peroxide (30% strength). Stirring is continued for 1.5 h under reflux, the reaction mixture is cooled and treated with half concentrated aqueous hydrochloric acid to adjust to pH 6-7. The solvents are evaporated and the residue is dried in vacuo to obtain 8.1 g of a yellowish solid, which can be used without further purification in the next step. The free acid is obtained by leaching the residue with boiling chloroform and concentration of the resulting chloroform solution.

13. (±)-(2SR,4aRS, 10bRS)-6-(3,4-Bis-cyclopropylmethoxyphenyl)-8,9-dimethoxy-(1,2,3,4,4a,10b)-hexahydrophenanthridin-2-ol 350 mg of (±)-acetic acid (2SR,4aRS,10bRS)-6-(3,4-bis-cyclopropylmethoxyphenyl)-8,9-dimethoxy-(1,2,3,4,4a,10b)-hexahydrophenanthridin-2-yl ester (compound 6) are dissolved in 3 ml of ethanol, treated with a solution of 180 mg of potassium hydroxide in 2.5 ml of water and the mixture is stirred for 10 min at 50° C. After 10 min the mixture is concentrated, the residue is redissolved in ethyl acetate and washed with water. The organic phase is dried using sodium sulfate and concentrated. The residue is crystallized from diethylether. 290 mg of the title compound of melting point 114-118° C. are obtained.

14. (±)-Acetic acid (2RS,4aRS,10bRS)-6-(4-butoxy-phenyl)-8,9-dimethoxy-1,2,3,4,4a,10b-hexahydro-phenanthridin-2-yl ester 1670 mg of phosphorous pentachloride are suspended in 2.5 ml of dichloromethane. 1119 mg of (±)-acetic acid (1RS,3RS,4RS)-4-{[1-(4-butoxy-phenyl)-methanoyl]-amino}-3-(3,4-dimethoxyphenyl)-cyclohexyl ester (compound A7) dissolved in 15 ml of dichloromethane are added and the mixture stirred for 18 h. The mixture is cooled to 0° C. and 10 ml of triethylamine added, then 5 ml of water. After phase separation and removal of solvent the solid residue is purified by flash chromatography [silica, toluene/dioxane=2:1 (containing 0.5% of ammonia)] to give 940 mg of the title compound as a colorless foam (87% of theory).

EF: $C_{27}H_{33}NO_5$; MW: 451.57
MS: 452.4 (MH$^+$)

Starting from the appropriate starting compounds, which are mentioned or described explicitly below, or which can be prepared in a manner known to the person skilled in the art or analogously or similarly to the below-described Examples, the following compounds are obtained according to the procedure as in

Example 14

15. (±)-Acetic acid (2RS,4aRS,10bRS)-8,9-dimethoxy-6-(4-methoxy-phenyl)-1,2,3,4,4a,10b-hexahydro-phenanthridin-2-yl ester

EF: $C_{24}H_{27}NO_5$; MW: 409.49
MS: 410.3 (MH$^+$)

16. (±)-Acetic acid (2RS,4aRS,10bRS)-6-(4-cyano-phenyl)-8,9-dimethoxy-1,2,3,4,4a,10b-hexahydro-phenanthridin-2-yl ester

EF: $C_{24}H_{24}N_2O_4$; MW: 404.47
MS: 405.3 (MH$^+$)

17. (±)-Acetic acid 4-((2RS,4aRS,10bRS)-2-acetoxy-8,9-dimethoxy-1,2,3,4,4a,10b-hexahydro-phenanthridin-6-yl)-phenyl ester

EF: $C_{25}H_{27}NO_6$; MW: 437.50
MS: 438.2 (MH$^+$)

18. (±)-Acetic acid (2RS,4aRS,10bRS)-6-(4-acetylamino-phenyl)-8,9-dimethoxy-1,2,3,4,4a,10b-hexahydro-phenanthridin-2-yl ester

EF: $C_{25}H_{28}N_2O_5$; MW: 436.51
MS: 437.3 (MH$^+$)

19. (±)-Acetic acid (2RS,4aRS,10bRS)-6-(4-chloro-phenyl)-8,9-dimethoxy-1,2,3,4,4a,10b-hexahydro-phenanthridin-2-yl ester EF: $C_{23}H_{24}ClNO_4$; MW: 413.91
MS: 414.3 (MH$^+$)

20. (±)-Acetic acid (2RS,4aRS,10bRS)-6-(2-chloro-phenyl)-8,9-dimethoxy-1,2,3,4,4a,10b-hexahydro-phenanthridin-2-yl ester EF: $C_{23}H_{24}ClNO_4$; MW: 413.91
MS: 414.3 (MH$^+$)

21. (±)-Acetic acid (2RS,4aRS,10bRS)-8,9-dimethoxy-6-(4-methoxy-3-propoxy-phenyl)-1,2,3,4,4a,10b-hexahydro-phenanthridin-2-yl ester

EF: $C_{27}H_{33}NO_6$; MW: 467.57
MS: 468.3 (MH$^+$)

22. (±)-Acetic acid (2RS,4aRS,10bRS)-8,9-dimethoxy-6-p-tolyl-1,2,3,4,4a,10b-hexahydro-phenanthridin-2-yl ester

EF: $C_{24}H_{27}NO_4$; MW: 393.49
MS: 394.3 (MH$^+$)

23. (±)-4-((2RS,4aRS,10bRS)-2-Acetoxy-9-ethoxy-8-methoxy-1,2,3,4,4a,10b-hexahydro-phenanthridin-6-yl)-benzoic acid methyl ester

EF: $C_{26}H_{29}NO_6$; MW: 451.52
MS: 452.4 (MH$^+$)

24. (±)-Acetic acid (2RS,4aRS,10bRS)-9-ethoxy-6-(4-fluoro-phenyl)-8-methoxy-1,2,3,4,4a,10b-hexahydro-phenanthridin-2-yl ester

EF: $C_{24}H_{26}FNO_4$; MW: 411.48
MS: 412.3 (MH$^+$)

25. (±)-Acetic acid (2RS,4aRS,10bRS)-6-(4-cyano-phenyl)-9-ethoxy-8-methoxy-1,2,3,4,4a,10b-hexahydro-phenanthridin-2-yl ester

EF: $C_{25}H_{26}N_2O_4$; MW: 418.50
MS: 419.3 (MH$^+$)

26. (±)-Acetic acid (2RS,4aRS,10bRS)-6-(3-cyclopropylmethoxy-4-ethoxy-phenyl)-9-ethoxy-8-methoxy-1,2,3,4,4a,10b-hexahydro-phenanthridin-2-yl ester

EF: $C_{30}H_{37}NO_6$; MW: 507.63
MS: 508.4 (MH$^+$)

27. (±)-Acetic acid (2RS,4aRS,10bRS)-6-[3-cyclopropylmethoxy-4-(1,1-difluoro-methoxy)-phenyl]-9-ethoxy-8-methoxy-1,2,3,4,4a,10b-hexahydro-phenanthridin-2-yl ester

EF: $C_{29}H_{33}F_2NO_6$; MW: 529.59
MS: 530.3 (MH$^+$)

28. (±)-Acetic acid (2RS,4aRS,10bRS)-6-[3,4-bis-(1,1-difluoro-methoxy)-phenyl]-9-ethoxy-8-methoxy-1,2,3,4,4a,10b-hexahydro-phenanthridin-2-yl ester

EF: $C_{26}H_{27}F_4NO_6$; MW: 525.50
MS: 526.3 (MH$^+$)

29. (±)-Acetic acid (2RS,4aRS,10bRS)-6-[3-(1,1-difluoro-methoxy)-phenyl]-9-ethoxy-8-methoxy-1,2,3,4,4a,10b-hexahydro-phenanthridin-2-yl ester

EF: $C_{25}H_{27}F_2NO_5$; MW: 459.49
MS: 460.2 (MH$^+$)

30. (±)-Acetic acid (2RS,4aRS,10bRS)-9-ethoxy-8-methoxy-6-[4-(1,1,2,2-tetrafluoro-ethoxy)-phenyl]-1,2,3,4,4a,10b-hexahydro-phenanthridin-2-yl ester

EF: $C_{26}H_{27}F_4NO_5$; MW: 509.50
MS: 510.2 (MH$^+$)

31. (±)-Acetic acid (2RS,4aRS,10bRS)-9-ethoxy-8-methoxy-6-(4-trifluoromethoxy-phenyl)-1,2,3,4,4a,10b-hexahydro-phenanthridin-2-yl ester

EF: $C_{25}H_{26}F_3NO_5$; MW: 477.48
MS: 478.2 (MH$^+$)

32. (±)-Acetic acid (2RS,4aRS,10bRS)-9-ethoxy-6-(3-fluoro-4-methoxy-phenyl)-8-methoxy-1,2,3,4,4a,10b-hexahydro-phenanthridin-2-yl ester

EF: $C_{25}H_{28}FNO_5$; MW: 441.50
MS: 442.2 (MH$^+$)

33. (±)-Acetic acid (2RS,4aRS,10bRS)-6-(3,4-difluoro-phenyl)-9-ethoxy-8-methoxy-1,2,3,4,4a,10b-hexahydro-phenanthridin-2-yl ester

EF: $C_{24}H_{25}F_2NO_4$; MW: 429.47
MS: 430.2 (MH$^+$)

34. (±)-Acetic acid (2RS,4aRS,10bRS)-9-ethoxy-6-(3-fluoro-phenyl)-8-methoxy-1,2,3,4,4a,10b-hexahydro-phenanthridin-2-yl ester

EF: $C_{24}H_{26}FNO_4$; MW: 411.48
MS: 412.2 (MH$^+$)

35. (±)-Acetic acid (2RS,4aRS,10bRS)-6-(4-bromo-phenyl)-9-ethoxy-8-methoxy-1,2,3,4,4a,10b-hexahydro-phenanthridin-2-yl ester EF: $C_{24}H_{26}BrNO_4$; MW: 472.38
MS: 472.2, 474.2 (MH$^+$)

36. (±)-Acetic acid (2RS,4aRS,10bRS)-6-[4-(1,1-difluoro-methoxy)-phenyl]-8,9-dimethoxy-1,2,3,4,4a,10b-hexahydro-phenanthridin-2-yl ester

EF: $C_{24}H_{25}F_2NO_5$; MW: 445.47
MS: 446.3 (MH$^+$)

37. (±)-Acetic acid (2RS,4aRS,10bRS)-8,9-dimethoxy-6-(4-phenoxy-phenyl)-1,2,3,4,4a,10b-hexahydro-phenanthridin-2-yl ester

EF: $C_{29}H_{29}NO_5$; MW: 471.56
MS: 472.3 (MH$^+$)

38. (±)-Acetic acid (2RS,4aRS,10bRS)-6-(4-fluoro-phenyl)-8,9-dimethoxy-1,2,3,4,4a,10b-hexahydro-phenanthridin-2-yl ester 39. (±)-Acetic acid (2RS,4aRS,10bRS)-6-[3,4-bis-(1,1-difluoro-methoxy)-phenyl]-8-(1,1-difluoro-methoxy)-9-methoxy-1,2,3,4,4a,10b-hexahydro-phenanthridin-2-yl ester

EF: $C_{25}H_{23}F_6NO_6$; MW: 547.46
MS: 548.3 (MH$^+$)

40. (±)-Acetic acid (2RS,4aRS, 10bRS)-6-(4-cyano-phenyl)-8-(1,1-difluoro-methoxy)-9-methoxy-1,2,3,4,4a,10b-hexahydro-phenanthridin-2-yl ester

EF: $C_{24}H_{22}F_2N_2O_4$; MW: 440.45
MS: 441.3 (MH$^+$)

41. (±)-4-[(2RS,4aRS,10bRS)-2-Acetoxy-8-(1,1-difluoro-methoxy)-9-methoxy-1,2,3,4,4a,10b-hexahydro-phenanthridin-6-yl]-benzoic acid methyl ester

EF: $C_{25}H_{25}F_2NO_6$; MW: 473.48
MS: 474.2 (MH$^+$)

42. (±)-4-[(2RS,4aRS,10bRS)-2-Acetoxy-9-(1,1-difluoro-methoxy)-8-methoxy-1,2,3,4,4a,10b-hexahydro-phenanthridin-6-yl]-benzoic acid methyl ester 500 mg of (±)-N-{(1RS,2RS,4RS)-4-acetoxy-2-[3-(1,1-difluoro-methoxy)-4-methoxy-phenyl]-cyclohexyl}-terephthalamic acid methyl ester (compound A35) are dissolved in 2 ml of phosphorus oxychloride and heated for 4.5 h at 100° C. After cooling to room temperature the sample is diluted with 10 ml of di-chloromethane and added dropwise to a aqueous sodium hydroxide solution. The water layer is extracted twice with dichloromethane. The solvent is removed and the crude product purified by chromatography on silica gel to give 310 mg of the title compound as a colourless foam.

EF: $C_{25}H_{25}F_2NO_6$; MW: 473.48
MS: 474.2 (MH$^+$)

43. (±)-(2RS,4aRS,10bRS)-6-(4-Butoxy-phenyl)-8,9-dimethoxy-1,2,3,4,4a,10b-hexahydrophenanthridin-2-ol 717 mg of (±)-acetic acid (2RS,4aRS,10bRS)-6-(4-butoxy-phenyl)-8,9-dimethoxy-1,2,3,4,4a,10b-hexahydro-phenanthridin-2-yl ester (compound 14) are dissolved in 8 ml of methanol and 1 ml of di-chloromethane, 259 mg of cesium carbonate are added and the mixture stirred for 19 h. The solvent is removed and the crude product is purified by flash chromatography (silica, ethyl acetate/triethylamine=9:1) to give 540 mg of the title compound as a colorless foam.

EF: $C_{25}H_{31}NO_4$; MW: 409.53
MS: 410.4 (MH$^+$)

Starting from the appropriate starting compounds mentioned or described in the abovementioned Examples, the following are obtained according to the procedure as in Example 43:

44. (±)-(2RS,4aRS,10bRS)-6-(4-Fluoro-phenyl)-8,9-dimethoxy-1,2,3,4,4a,10b-hexahydro-phenanthridin-2-ol

EF: $C_{21}H_{22}FNO_3$; MW: 355.41
MS: 356.4 (MH$^+$)

45. (±)-N-[4-((2RS,4aRS,10bRS)-2-Hydroxy-8,9-dimethoxy-1,2,3,4,4a,10b-hexahydro-phenanthridin-6-yl)-phenyl]-acetamide

EF: $C_{23}H_{26}N_2O_4$; MW: 394.47
MS: 395.4 (MH$^+$)

46. (±)-(2RS,4aRS,10bRS)-6-(4-Chloro-phenyl)-8,9-dimethoxy-1,2,3,4,4a,10 b-hexahydro-phenanthridin-2-ol EF: $C_{21}H_{22}ClNO_3$; MW: 371.87
MS: 372.4 (MH$^+$)

47. (±)-(2RS,4aRS,10bRS)-6-(2-Chloro-phenyl)-8,9-dimethoxy-1,2,3,4,4a,10b-hexahydro-phenanthridin-2-ol EF: $C_{21}H_{22}ClNO_3$; MW: 371.87
MS: 372.4 (MH$^+$)

48. (±)-(2RS,4aRS,10bRS)-8,9-Dimethoxy-6-(4-methoxy-3-propoxy-phenyl)-1,2,3,4,4a,10b-hexahydro-phenanthridin-2-ol

EF: $C_{25}H_{31}NO_5$; MW: 425.53
MS: 426.4 (MH$^+$)

49. (±)-(2RS,4aRS,10bRS)-6-[4-(1,1-Difluoro-methoxy)-phenyl]-8,9-dimethoxy-1,2,3,4,4a,10b-hexahydro-phenanthridin-2-ol

EF: $C_{22}H_{23}F_2NO_4$; MW: 403.43
MS: 404.3 (MH$^+$)

50. (±)-4-((2RS,4aRS,10bRS)-9-Ethoxy-2-hydroxy-8-methoxy-1,2,3,4,4a,10 b-hexahydro-phenanthridin-6-yl)-benzoic acid methyl ester

EF: $C_{24}H_{27}NO_5$; MW: 409.49
MS: 410.3 (MH$^+$)

51. (±)-(2RS,4aRS,10bRS)-9-Ethoxy-6-(4-fluoro-phenyl)-8-methoxy-1,2,3,4,4a,10b-hexahydro-phenanthridin-2-ol

EF: $C_{22}H_{24}FNO_3$; MW: 369.44
MS: 370.3 (MH$^+$)

52. (±)-4-((2RS,4aRS,10bRS)-9-Ethoxy-2-hydroxy-8-methoxy-1,2,3,4,4a,10b-hexahydro-phenanthridin-6-yl)-benzonitrile

EF: $C_{23}H_{24}N_2O_3$; MW: 376.46
MS: 377.3 (MH$^+$)

53. (±)-(2RS,4aRS,10bRS)-6-(3-Cyclopropyl-methoxy-4-ethoxy-phenyl)-9-ethoxy-8-methoxy-1,2,3,4,4a,10b-hexahydro-phenanthridin-2-ol

EF: $C_{28}H_{35}NO_5$; MW: 465.59
MS: 466.4 (MH$^+$)

54. (±)-(2RS,4aRS,10bRS)-6-[3-Cyclopropyl-methoxy-4-(1,1-difluoro-methoxy)-phenyl]-9-ethoxy-8-methoxy-1,2,3,4,4a,10b-hexahydro-phenanthridin-2-ol

EF: $C_{27}H_{31}F_2NO_5$; MW: 487.55
MS: 488.4 (MH$^+$)

55. (±)-(2RS,4aRS,10bRS)-6-[3,4-Bis-(1,1-difluoro-methoxy)-phenyl]-9-ethoxy-8-methoxy-1,2,3,4,4a,10b-hexahydro-phenanthridin-2-ol

EF: $C_{24}H_{25}F_4NO_5$; MW: 483.46
MS: 484.3 (MH$^+$)

56. (±)-(2RS,4aRS,10bRS)-6-[3-(1,1-Difluoro-methoxy)-phenyl]-9-ethoxy-8-methoxy-1,2,3,4,4a,10b-hexahydro-phenanthridin-2-ol

EF: $C_{23}H_{25}F_2NO_4$; MW: 417.46
MS: 418.3 (MH$^+$)

57. (±)-(2RS,4aRS,10bRS)-9-Ethoxy-8-methoxy-6-[4-(1,1,2,2-tetrafluoro-ethoxy)-phenyl]-1,2,3,4,4a,10b-hexahydro-phenanthridin-2-ol

EF: $C_{24}H_{25}F_4NO_4$; MW: 467.46
MS: 468.2 (MH$^+$)

58. (±)-(2RS,4aRS,10bRS)-9-Ethoxy-8-methoxy-6-(4-trifluoromethoxy-phenyl)-1,2,3,4,4a,10b-hexahydro-phenanthridin-2-ol

EF: $C_{23}H_{24}F_3NO_4$; MW: 435.45
MS: 436.3 (MH$^+$)

59. (±)-(2RS,4aRS,10bRS)-9-Ethoxy-6-(3-fluoro-4-methoxy-phenyl)-8-methoxy-1,2,3,4,4a,10b-hexahydro-phenanthridin-2-ol

EF: $C_{23}H_{26}FNO_4$; MW: 399.47
MS: 400.3 (MH$^+$)

60. (±)-(2RS,4aRS,10bRS)-6-(3,4-Difluoro-phenyl)-9-ethoxy-8-methoxy-1,2,3,4,4a,10b-hexahydro-phenanthridin-2-ol

EF: $C_{22}H_{23}F_2NO_3$; MW: 387.43
MS: 388.2 (MH$^+$)

61. (±)-(2RS,4aRS, 10bRS)-9-Ethoxy-6-(3-fluoro-phenyl)-8-methoxy-1,2,3,4,4a,10b-hexahydro-phenanthridin-2-ol

EF: $C_{22}H_{24}FNO_3$; MW: 369.44
MS: 370.2 (MH$^+$)

62. (±)-(2RS,4aRS,10bRS)-6-(4-Bromo-phenyl)-9-ethoxy-8-methoxy-1,2,3,4,4a,10b-hexahydro-phenanthridin-2-ol EF: $C_{22}H_{24}BrNO_3$; MW: 430.35
MS: 430.2, 432.2 (MH$^+$)

63. (±)-(2RS,4aRS,10bRS)-8,9-Dimethoxy-6-p-tolyl-1,2,3,4,4a,10b-hexahydro-phenanthridin-2-ol

EF: $C_{22}H_{25}NO_3$; MW: 351.45
MS: 352.4 (MH$^+$)

64. (±)-(2RS,4aRS,10bRS)-8,9-Dimethoxy-6-(4-phenoxy-phenyl)-1,2,3,4,4a,10b-hexahydro-phenanthridin-2-ol

EF: $C_{27}H_{27}NO_4$; MW: 429.52
MS: 430.4 (MH$^+$)

65. (±)-(2RS,4aRS, 10bRS)-8,9-Dimethoxy-6-(4-methoxy-phenyl)-1,2,3,4,4a,10b-hexahydro-phenanthridin-2-ol 66. (±)-4-((2RS,4aRS,10bRS)-2-Hydroxy-8,9-dimethoxy-1,2,3,4,4a,10b-hexahydro-phenanthridin-6-yl)-benzonitrile 67. (±)-(2RS,4aRS,10bRS)-6-[3,4-Bis-(1,1-difluoro-methoxy)-phenyl]-8-(1,1-difluoro-methoxy)-9-methoxy-1,2,3,4,4a,10b-hexahydro-phenanthridin-2-ol

EF: $C_{23}H_{21}F_6NO_5$; MW: 505.42
MS: 506.3 (MH$^+$)

68. (±)-4-[(2RS,4aRS,10bRS)-8-(1,1-Difluoro-methoxy)-2-hydroxy-9-methoxy-1,2,3,4,4a,10b-hexahydro-phenanthridin-6-yl]-benzonitrile

EF: $C_{22}H_{20}F_2N_2O_3$; MW: 398.41
MS: 399.3 (MH$^+$)

69. (±)-4-[(2RS,4aRS,10bRS)-8-(1,1-Difluoro-methoxy)-2-hydroxy-9-methoxy-1,2,3,4,4a,10b-hexahydro-phenanthridin-6-yl]-benzoic acid methyl ester

EF: $C_{23}H_{23}F_2NO_5$; MW: 431.44
MS: 432.3 (MH$^+$)

70. (±)-4-[(2RS,4aRS,10bRS)-9-(1,1-Difluoro-methoxy)-2-hydroxy-8-methoxy-1,2,3,4,4a,10b-hexahydro-phenanthridin-6-yl]-benzoic acid methyl ester

EF: $C_{23}H_{23}F_2NO_5$; MW: 431.44
MS: 432.3 (MH$^+$)

71. (±)-Acetic acid (2RS,4aRS,10bRS)-6-(4-hydroxy-phenyl)-8,9-dimethoxy-1,2,3,4,4a,10b-hexahydro-phenanthridin-2-yl ester Starting from compound 17, the acetyl group bonded to the phenoxy ring is removed by a procedure as in Example 43.
EF: $C_{23}H_{25}NO_5$; MW: 395.46
MS: 396.3 (MH$^+$)

72. (±)-4-((2RS,4aRS,10bRS)-2-Acetoxy-8,9-dimethoxy-1,2,3,4,4a,10b-hexahydro-phenanthridin-6-yl)-benzoic acid hydrochloride 8.1 g of (±)-(2RS,4aRS,10bRS)-6-(4-carboxyphenyl)-8,9-dimethoxy-(1,2,3,4,4a,10b)-hexahydro-phenanthridin-2-ol (compound 12) are suspended in 35 ml of dichloromethane and 40 ml of acetyl chloride are added dropwise. After stirring for 1 h at room temperature, the mixture is concentrated and the residue is dissolved in aqueous 1 M disodium hydrogenphosphate solution at pH 6-7. Under stirring concentrated hydrochloric acid is added, the resulting precipitate is filtered off and dried in vacuo to give 4.65 g of the title compound as beige hydrochloride salt.

The free acid is obtained by dissolving the hydrochloride salt in water at pH 6-7, removal of the solvent in vacuo, leaching the resulting yellowish residue with boiling chloroform and concentration of the obtained chloroform solution.
EF: $C_{24}H_{25}NO_6$; MW: 423.47
MS: 424.3 (MH$^+$)

73. (±)-4-((2RS,4aRS,10bRS)-2-Acetoxy-9-(1,1-difluoro-methoxy)-8-methoxy-1,2,3,4,4a,10b-hexahydro-phenanthridin-6-yl)-benzoic acid The title compound is obtained in two steps starting from compound 42 by saponification analogously as described in Example 12 followed by acetylation of obtained intermediate (±)-(2RS,4aRS,10bRS)-6-(4-carboxyphenyl)-9-(1,1-difluoro-methoxy)-8-methoxy-(1,2,3,4,4a,10b)-hexahydro-phenanthridin-2-ol analogously as described in Example 72.
EF: $C_{24}H_{23}F_2NO_6$; MW: 459.45
MS: 460.3 (MH$^+$)

74. (±)-(2RS,4aRS,10bRS)-6-(3,4-Bis-cyclopropyl-methoxy-phenyl)-2,8,9-trimethoxy-1,2,3,4,4a,10b-hexahydro-phenanthridine 240 mg of (±)-(2RS,4aRS,10bRS)-6-(3,4-bis-cyclopropylmethoxyphenyl)-8,9-dimethoxy-(1,2,3,4,4a,10b)-hexahydrophenanthridin-2-ol (compound 7) are dissolved in 2.5 ml of tetrahydrofurane and 140 mg of potassium-tert-butoxide are added. Then 0.6 g of methyl iodide dissolved in 0.5 ml of tetrahydrofurane are added and the reaction mixture stirred until the reaction is complete. Work-up with water followed by extraction with dichloromethane gives after purification by chromatography on silica gel 164 mg of the title compound as a colorless foam.
EF: $C_{30}H_{37}NO_5$; MW: 491.63
MS: 492.4 (MH$^+$)

75. (±)-(2RS,4aRS,10bRS)-6-(3,4-Bis-cyclopropyl-methoxy-phenyl)-2-ethoxy-8,9-dimethoxy-1,2,3,4,4a,10b-hexahydro-phenanthridine Starting from (±)-(2RS,4aRS,10bRS)-6-(3,4-bis-cyclopropylmethoxyphenyl)-8,9-dimethoxy-(1,2,3,4,4a,10b)-hexahydrophenanthridin-2-ol (compound 7) the title compound is obtained analogously to the procedure as in Example 74 using ethyl iodide as alkylating reagent at 70° C.
EF: $C_{31}H_{39}NO_5$; MW: 505.66
MS: 506.4 (MH$^+$)

76. (±)-(2RS,4aRS,10bRS)-6-(3,4-Bis-cyclopropyl-methoxy-phenyl)-8,9-dimethoxy-2-(2-methoxy-ethoxy)-1,2,3,4,4a,10b-hexahydro-phenanthridine Starting from (±)-(2RS,4aRS,10bRS)-6-(3,4-bis-cyclopropylmethoxyphenyl)-8,9-dimethoxy-(1,2,3,4,4a,10b)-hexahydrophenanthridin-2-ol (compound 7) the title compound is obtained analogously to the procedure as in Example 74 using methoxyethyl triflate as alkylating reagent at 70° C.
EF: $C_{32}H_{41}NO_6$; MW: 535.69
MS: 536.4 (MH$^+$)

Starting Compounds:

A1. (±)-Acetic acid (1RS,3RS,4RS)-4-{[1-(3,4-bis-cyclopropylmethoxyphenyl)methanoyl]-amino}-3-(3,4-dimethoxyphenyl)cyclohexyl ester 590 mg of (±)-acetic acid (1RS,3RS,4RS)-4-amino-3-(3,4-dimethoxyphenyl)cyclohexyl ester (compound B1) are dissolved in a mixture of 6 ml of methylene chloride and 1.5 ml of pyridine and 10 mg of 4-dimethylaminopyridine are added. A solution of 595 mg of 3,4-dicyclopropylmethoxybenzoyl chloride in methylene chloride is added dropwise and the mixture is stirred for 16 h. Further 140 mg of dicyclopropylmethoxybenzoyl chloride and 10 mg of 4-dimethylaminopyridine are added to complete the reaction. The solvents are removed and the residue is purified by chromatography on silica gel using a mixture of petroleum ether/ethyl acetate/triethylamine in the ratio 5/4/1 as eluent. After concentration of the corresponding eluate fractions, 630 mg (59% of theory) of the title compound are obtained as a colourless foam.
EF: $C_{31}H_{39}NO_7$; MW: 537.66
MS: 538.2 (MH$^+$), 560.3 (MNa$^+$)
$R_f$=0.57 (petroleum ether/ethyl acetate/triethylamine=6/3/1)
S.p.: 70-75° C.
M.p.: 136-137° C.

A2. (±)-Acetic acid (1RS,3RS,4RS)-4-{[1-(4-methoxycarbonylphenyl)methanoyl]amino}-3-(3,4-dimethoxyphenyl)cyclohexyl ester 1.6 g of (±)-acetic acid (1RS,3RS,4RS)-4-amino-3-(3,4-dimethoxyphenyl)cyclohexyl ester (compound B1) are dissolved in 30 ml of dichloromethane. 982 mg (5.45 mmol) of terephthalic acid monomethyl ester and 1.25 g (6.74 mmol) of N-ethyl-N'-(3-dimethylaminopropyl)carbodiimide hydrochloride are added successively under stirring. After 3 h further 18 mg (0.1 mmol) of terephthalic acid monomethyl ester are added. After 15 h the reaction is treated with aqueous hydrochloric acid and extracted several times with dichloromethane. After evaporation of the combined organic phases, the crude product is crystallized from ethyl acetate/cyclohexane to give 1.87 g (73% of theory) of the title compound as colourless solid.
EF: $C_{25}H_{29}NO_7$; MW: 455.51
MS: 456.2 (MH$^+$)
$R_f$=0.69 (ethyl acetate/triethylamine=9/1)

Starting from the starting compounds described below, the following are obtained according to the procedures as in Example A1 or in Example A2:

A3. (±)-Acetic acid (1RS,3RS,4RS)-4-{[1-(4-dimethylaminophenyl)methanoyl]amino}-3-(3,4-dimethoxyphenyl)cyclohexyl ester EF: $C_{25}H_{32}N_2O_5$; MW: 440.54
MS: 441.2 (MH$^+$), 463.2 (MNa$^+$)
$R_f$=0.50 (ethyl acetate/triethylamine=9/1)

A4. (±)-Acetic acid (1RS,3RS,4RS)-4-{[1-(3,4-dimethyoxyphenyl)methanoyl]amino}-3-(3,4-di-methoxyphenyl)cyclohexyl ester EF: $C_{25}H_{31}NO_7$; MW: 457.53
MS: 458.1 (MH$^+$), 480.3 (MNa$^+$)
$R_f$=0.15 (petroleum ether/ethyl acetate/triethylamine=5/4/1)
M.p.: 70-78° C.

A5. (±)-Acetic acid (1RS,3RS,4RS)-4-{[1-(4-nitrophenyl)methanoyl]amino}-3-(3,4-dimethoxy-phenyl)cyclohexyl ester EF: $C_{23}H_{26}N_2O_7$; MW: 442.47
MS: 443.1 (MH$^+$)
$R_f$=0.31 (petroleum ether/ethyl acetate=1/1)
M.p.: 83-94° C.

A6. (±)-Acetic acid (1SR,3RS,4RS)-4-{[1-(3,4-bis-cyclopropylmethoxyphenyl)methanoyl]-amino}-3-(3,4-dimethoxyphenyl)cyclohexyl ester 9.5 mmol of (±)-acetic acid (1SR,3RS,4RS)-4-amino-3-(3,4-dimethoxyphenyl)cyclohexyl ester (compound B2) are dissolved in a mixture of 40 ml of methylene chloride and 10 ml of triethylamine and treated with 8.9 mmol of 3,4-dicyclopropylmethoxybenzoyl chloride.

After stirring for 1 h at room temperature, the reaction mixture is concentrated and the residue chromatographed on silica gel using a mixture of petroleum ether/ethyl acetate/triethylamine in the ratio 4/4/1 as eluent. After concentration of the corresponding eluate fractions, 1.86 mmol of the title compound are obtained.

A7. (±)-Acetic acid (1RS,3RS,4RS)-4-{[1-(4-butoxy-phenyl)-methanoyl]-amino}-3-(3,4-dimethoxy-phenyl)-cyclohexyl ester 790 mg of (±)-acetic acid (1RS,3RS,4RS)-4-amino-3-(3,4-dimethoxyphenyl)cyclohexyl ester (compound B1), 620 mg of 4-butoxybenzoic acid, 614 mg of N-ethyl-N'-(3-dimethylaminopropyl)carbodiimide hydrochloride and 2 mg of 4-dimethylaminopyridine are stirred in 7 ml of dichloromethane for 18 h. 5 ml of water are added, the phases are separated and once the organic layer is extracted with 3 ml of dichloromethane. Then the organic layer is washed with 2.5 ml of saturated aqueous potassium bicarbonate solution and the aqueous solution is once extracted with 5 ml of dichloromethane. The combined organic layers are dried over magnesium sulfate, then the solvent is removed to give 1172 mg of the title compound as a colorless foam.

EF: $C_{27}H_{35}NO_6$; MW: 469.58
MS: 470.2 ($MH^+$)

Starting from the appropriate starting compounds, which are mentioned or described explicitly below, or which can be prepared in a manner known to the person skilled in the art or analogously or similarly to the Examples described herein, the following and also further relevant, non-explicitly described similar compounds are obtained according to the procedure as in Example A7:

A8. (±)-Acetic acid (1RS,3RS,4RS)-3-(3,4-dimethoxy-phenyl)-4-{[1-(4-fluoro-phenyl)-methanoyl]-amino}-cyclohexyl ester

EF: $C_{23}H_{26}FNO_5$; MW: 415.47

A9. (±)-Acetic acid (1RS,3RS,4RS)-4-{[1-(4-acetoxy-phenyl)-methanoyl]-amino}-3-(3,4-dimethoxy-phenyl)-cyclohexyl ester

EF: $C_{25}H_{29}NO_7$; MW: 455.51
MS: 456.1 ($MH^+$)

A10. (±)-Acetic acid (1RS,3RS,4RS)-4-{[1-(4-acetylamino-phenyl)-methanoyl]-amino}-3-(3,4-dimethoxy-phenyl)-cyclohexyl ester

EF: $C_{25}H_{30}N_2O_6$; MW: 454.53
MS: 455.1 ($MH^+$)

A11. (±)-Acetic acid (1RS,3RS,4RS)-4-{[1-(4-chloro-phenyl)-methanoyl]-amino}-3-(3,4-dimethoxy-phenyl)-cyclohexyl ester EF: $C_{23}H_{26}ClNO_5$; MW: 431.92
MS: 432.1 ($MH^+$)

A12. (±)-Acetic acid (1RS,3RS,4RS)-4-{[1-(2-chloro-phenyl)-methanoyl]-amino}-3-(3,4-dimethoxy-phenyl)-cyclohexyl ester EF: $C_{23}H_{26}ClNO_5$; MW: 431.92
MS: 432.1 ($MH^+$)

A13. (±)-Acetic acid (1RS,3RS,4RS)-3-(3,4-dimethoxy-phenyl)-4-{[1-(4-phenoxy-phenyl)-methanoyl]-amino}-cyclohexyl ester

EF: $C_{29}H_{31}NO_6$; MW: 489.57
MS: 490.1 ($MH^+$)

A14. (±)-Acetic acid (1RS,3RS,4RS)-3-(3,4-dimethoxy-phenyl)-4-{[1-(4-methoxy-3-propoxy-phenyl)-methanoyl]-amino}-cyclohexyl ester

EF: $C_{27}H_{35}NO_7$; MW: 485.58
MS: 486.2 ($MH^+$)

A15. (±)-Acetic acid (1RS,3RS,4RS)-3-(3,4-dimethoxy-phenyl)-4-[(1-p-tolyl-methanoyl)-amino]-cyclohexyl ester

EF: $C_{24}H_{29}NO_5$; MW: 411.5
MS: 412.2 ($MH^+$)

A16. (±)-Acetic acid (1RS,3RS,4RS)-4-({1-[4-(1,1-difluoro-methoxy)-phenyl]-methanoyl}-amino)-3-(3,4-dimethoxy-phenyl)-cyclohexyl ester

EF: $C_{24}H_{27}F_2NO_6$; MW: 463.48
MS: 464.1 ($MH^+$)

A17. (±)-N-[(1RS,2RS,4RS)-4-Acetoxy-2-(3-ethoxy-4-methoxy-phenyl)-cyclohexyl]-terephthalamic acid methyl ester

EF: $C_{26}H_{31}NO_7$; MW: 469.54
MS: 470.1 ($MH^+$)

A18. (±)-Acetic acid (1RS,3RS,4RS)-3-(3-ethoxy-4-methoxy-phenyl)-4-{[1-(4-fluoro-phenyl)-methanoyl]-amino}-cyclohexyl ester

EF: $C_{24}H_{28}FNO_5$; MW: 429.49
MS: 430.1 ($MH^+$)

A19. (±)-Acetic acid (1RS,3RS,4RS)-4-{[1-(4-cyano-phenyl)-methanoyl]-amino}-3-(3-ethoxy-4-methoxy-phenyl)-cyclohexyl ester

EF: $C_{25}H_{25}N_2O_5$; MW: 436.51
MS: 437.1 ($MH^+$)

A20. (±)-Acetic acid (1RS,3RS,4RS)-4-{[1-(3-cyclopropylmethoxy-4-ethoxy-phenyl)-methanoyl]-amino}-3-(3-ethoxy-4-methoxy-phenyl)-cyclohexyl ester

EF: $C_{30}H_{39}NO_7$; MW: 525.65
MS: 526.2 (MH$^+$)

A21. (±)-Acetic acid (1RS,3RS,4RS)-4-({1-[3-cyclopropylmethoxy-4-(1,1-difluoro-methoxy)-phenyl]-methanoyl}-amino)-3-(3-ethoxy-4-methoxy-phenyl)-cyclohexyl ester

EF: $C_{29}H_{35}F_2NO_7$; MW: 547.6
MS: 548.2 (MH$^+$)

A22. (±)-Acetic acid (1RS,3RS,4RS)-4-({1-[3,4-bis-(1,1-difluoro-methoxy)-phenyl]-methanoyl}-amino)-3-(3-ethoxy-4-methoxy-phenyl)-cyclohexyl ester

EF: $C_{26}H_{29}F_4NO_7$; MW: 543.52
MS: 544.1 (MH$^+$)

A23. (±)-Acetic acid (1RS,3RS,4RS)-3-(3,4-dimethoxy-phenyl)-4-{[1-(4-methoxy-phenyl)-methanoyl]-amino}-cyclohexyl ester A24. (±)-Acetic acid (1RS,3RS,4RS)-3-(3,4-dimethoxy-phenyl)-4-{[1-(4-cyano-phenyl)-methanoyl]-amino}-cyclohexyl ester A25. (±)-Acetic acid (1RS,3RS,4RS)-4-({1-[3-(1,1-difluoro-methoxy)-phenyl]-methanoyl}-amino)-3-(3-ethoxy-4-methoxy-phenyl)-cyclohexyl ester A26. (±)-Acetic acid (1RS,3RS,4RS)-4-({1-[4-(1,1,2,2-tetrafluoro-ethoxy)-phenyl]-methanoyl}-amino)-3-(3-ethoxy-4-methoxy-phenyl)-cyclohexyl ester A27. (±)-Acetic acid (1RS,3RS,4RS)-4-({1-[4-(trifluoro-methoxy)-phenyl]-methanoyl}-amino)-3-(3-ethoxy-4-methoxy-phenyl)-cyclohexyl ester A28. (±)-Acetic acid (1RS,3RS,4RS)-4-({1-[3-fluoro-4-methoxy-phenyl]-methanoyl}-amino)-3-(3-ethoxy-4-methoxy-phenyl)-cyclohexyl ester A29. (±)-Acetic acid (1RS,3RS,4RS)-4-({1-[3,4-difluoro-phenyl]-methanoyl}-amino)-3-(3-ethoxy-4-methoxy-phenyl)-cyclohexyl ester A30. (±)-Acetic acid (1RS,3RS,4RS)-4-({1-[3-fluoro-phenyl]-methanoyl}-amino)-3-(3-ethoxy-4-methoxy-phenyl)-cyclohexyl ester A31. (±)-Acetic acid (1RS,3RS,4RS)-4-(1-[4-bromo-phenyl]-methanoyl)-amino)-3-(3-ethoxy-4-methoxy-phenyl)-cyclohexyl ester A32. (±)-Acetic acid (1RS,3RS,4RS)-4-({1-[3,4-bis-(1,1-difluoro-methoxy)-phenyl]-methanoyl}-amino)-3-[4-(1,1-difluoro-methoxy)-3-methoxy-phenyl]-cyclohexyl ester

EF: $C_{25}H_{25}F_6NO_7$; MW: 565.47
MS: 566.0 (MH$^+$)

A33. (±)-Acetic acid (1RS,3RS,4RS)-4-{[1-(4-cyano-phenyl)-methanoyl]-amino}-3-[4-(1,1-difluoro-methoxy)-3-methoxy-phenyl]-cyclohexyl ester

EF: $C_{24}H_{24}F_2N_2O_5$; MW: 458.47
MS: 459.0 (MH$^+$)

A34. (±)-N-{(1RS,2RS,4RS)-4-Acetoxy-2-[4-(1,1-difluoro-methoxy)-3-methoxy-phenyl]-cyclohexyl}-terephthalamic acid methyl ester A35. (±)-N-{(1RS,2RS,4RS)-4-Acetoxy-2-[3-(1,1-difluoro-methoxy)-4-methoxy-phenyl]-cyclohexyl}-terephthalamic acid methyl ester

EF: $C_{25}H_{27}F_2NO_7$; MW: 491.49
MS: 492.0 (MH$^+$)

B1. (±)-Acetic acid (1RS,3RS,4RS)-4-amino-3-(3,4-dimethoxyphenyl)cyclohexyl ester A solution of 10.37 g of (±)-acetic acid (1RS,3RS,4RS)-3-(3,4-dimethoxyphenyl)-4-nitrocyclohexyl ester (compound C1) in 240 ml of ethanol is added to a zinc-copper couple, prepared from 16.8 g of zinc powder and 920 mg of copper (II) acetate monohydrate in acetic acid, the resulting suspension is refluxed and treated with 26 ml of acetic acid, 3.2 ml of water and 26 ml of ethanol. The resulting mixture is refluxed for further 15 min. The precipitate is filtered off with suction and the solvent is removed. Chromatographical purification on silica gel using a mixture of petroleum ether/ethyl acetate/triethylamine in the ratio 2/7/1 and concentration of the corresponding eluate fractions afford 5.13 g (55% of theory) of the title compound as a pale brown oil.

$R_f$=0.35 (petroleum ether/ethyl acetate/triethylamine=2/7/1)

B2. (±)-Acetic acid (1SR,3RS,4RS)-4-amino-3-(3,4-dimethoxyphenyl)cyclohexyl ester 2.1 g of (±)-acetic acid (1SR,3RS,4RS)-3-(3,4-dimethoxyphenyl)-4-nitrocyclohexyl ester (compound C5) are dissolved in 50 ml of ethanol and treated with 2 g of zinc powder. 5 ml of acetic acid are added dropwise at boiling heat. After 1 h the reaction mixture is filtered and the filtrate is concentrated. The residue is used without further purification for the next step.

Starting from the appropriate starting compounds, which are mentioned or described explicitly below, or which can be prepared in a manner known to the person skilled in the art or analogously or similarly to the Examples described herein, the following and also further relevant, non-explicitly described similar compounds are obtained according to the procedures as in Examples B1 or B2:

B3. (±)-Acetic acid (1RS,3RS,4RS)-4-amino-3-(3-ethoxy-4-methoxy-phenyl)-cyclohexyl ester

EF: $C_{17}H_{25}NO_4$; MW: 307.39
MS: 308.0 (MH$^+$)

B4. (±)-Acetic acid (1RS,3RS,4RS)-4-amino-3-[3-(1,1-difluoro-methoxy)-4-methoxy-phenyl]-cyclohexyl ester

EF: $C_{16}H_{21}F_2NO_4$; MW: 329.35
MS: 330.0 (MH$^+$)

B5. (±)-Acetic acid (1RS,3RS,4RS)-4-amino-3-[4-(1,1-difluoro-methoxy)-3-methoxy-phenyl]-cyclohexyl ester

EF: C₁₆H₂₁F₂NO₄; MW: 329.35
MS: 330.0 (MH⁺)

C1. (±)-Acetic acid (1RS,3RS,4RS)-3-(3,4-dimethoxyphenyl)-4-nitrocyclohexyl ester 10.18 g of (±)-(1RS,3RS,4RS)-3-(3,4-dimethoxyphenyl)-4-nitrocyclohexanol (compound D1) are dissolved in 100 ml of acetic anhydride and the solution is heated to 100° C. for 1-2 h. After removal of the solvent, the residue is chromatographed on silica gel using a mixture of petroleum ether/ethyl acetate in the ratio 2/1. Concentration of the corresponding eluate fractions furnish 10.37 g (89% of theory) of the title compound as an oil.

$R_f$=0.32 (petroleum ether/ethyl acetate=2/1)

Starting from the starting compounds mentioned below, the following are obtained according to the procedure as in Example C1:

C2. (±)-Acetic acid (1RS,3RS,4RS)-3-(3-ethoxy-4-methoxy-phenyl)-4-nitrocyclohexyl ester C3. (±)-Acetic acid (1RS,3RS,4RS)-3-[3-(1,1-difluoro-methoxy)-4-methoxy-phenyl]-4-nitrocyclohexyl ester C4. (±)-Acetic acid (1RS,3RS,4RS)-3-[4-(1,1-difluoro-methoxy)-3-methoxy-phenyl]-4-nitrocyclohexyl ester C5. (±)-Acetic acid (1SR,3RS,4RS)-3-(3,4-dimethoxyphenyl)-4-nitrocyclohexyl ester 7.0 g of (±)-acetic acid (1SR,3RS,4SR)-3-(3,4-dimethoxyphenyl)-4-nitrocyclohexyl ester (compound D5) are dissolved in 100 ml of absolute 1,2-dimethoxyethane and treated with 8.2 ml of a 30% solution of sodium methanolate in methanol at room temperature. A solution of 2 ml of conc. sulfuric acid in 8 ml of absolute ethanol is then added dropwise under cooling in an ice bath. After stirring for 1 h the cooling bath is removed, the mixture is diluted with 200 ml of water, and extracted with ethyl acetate. The organic layer is dried over sodium sulfate and concentrated. The residue is used in the next step without further purification.

5.8 g of the said residue are dissolved in 40 ml of acetic anhydride and the solution is stirred at 100° C. for 3 h. The reaction mixture is concentrated and the residue is purified by chromatography on silica gel using a mixture of petroleum ether/ethyl acetate in the ratio 1/1. The solvents of the corresponding eluate fractions are evaporated to furnish 2.2 g of the title compound of melting point 113-115° C.

D1. (±)-(1RS,3RS,4RS)-3-(3,4-Dimethoxyphenyl)-4-nitrocyclohexanol 10 g of (±)-(1RS,3RS,4SR)-3-(3,4-dimethoxyphenyl)-4-nitrocyclohexanol (compound E1) are dissolved in 170 ml of absolute 1,2-dimethoxyethane. 14.3 ml of a 30% solution of sodium methanolate in methanol are added dropwise. After complete addition, stirring is continued for 10 min and a mixture consisting of 85% phosphoric acid and methanol is added to pH 1. By adding of saturated potassium hydrogencarbonate solution the resulting suspension is neutralized. The mixture is diluted with water and di-chloromethane, the organic layer is separated and extracted with dichloromethane. The solvents are removed under reduced pressure to yield the title compound as a pale yellow oil, which crystallizes. The title compound is used without further purification in the next step.

$R_f$=0.29 (petroleum ether/ethyl acetate=1/1)
M.p.: 126-127° C.

Starting from the appropriate starting compounds mentioned below, the following are obtained according to the procedure as in Example D1:

D2. (±)-(1RS,3RS,4RS)-3-(3-Ethoxy-4-methoxy-phenyl)-4-nitrocyclohexanol

D3. (±)-(1RS,3RS,4RS)-3-[3-(1,1-Difluoro-methoxy)-4-methoxy-phenyl]-4-nitrocyclohexanol D4. (±)-(1RS,3RS,4RS)-3-[4-(1,1-Difluoro-methoxy)-3-methoxy-phenyl]-4-nitrocyclohexanol D5. (±)-Acetic acid (1SR,3RS,4SR)-3-(3,4-Dimethoxyphenyl)-4-nitrocyclohexyl ester 6.0 g of (±)-(1SR,3RS,4SR)-3-(3,4-dimethoxyphenyl)-4-nitrocyclohexanol (compound E5) are dissolved in 40 ml of acetic anhydride and stirred for 1.5 h at 100° C. The reaction mixture is concentrated and the residual title compound of melting point 108-110° C. is used without further purification in the next step.

E1. (±)-(1RS,3RS,4SR)-3-(3,4-Dimethoxyphenyl)-4-nitrocyclohexanol

Under nitrogen atmosphere 16.76 g of (±)-(3RS,4SR)-3-(3,4-dimethoxyphenyl)-4-nitrocyclohexanone (compound F1) are dissolved in 300 ml of tetrahydrofurane, the solution is cooled to −78° C., and 75 ml of 1 M solution of potassium tri-sec-butylborohydride in tetrahydrofurane is added dropwise. After stirring for further 1 h, a mixture consisting of 30% hydrogeneperoxide solution and phosphate buffer solution is added. Stirring is continued for further 10 min, the reaction mixture is diluted with 400 ml of ethyl acetate and the aqueous layer is extracted with ethyl acetate, the combined organic phases are concentrated to give a foam, which is purified by chromatography on silica gel using a mixture of petroleum ether/ethyl acetate in the ratio 1/1 to furnish 10.18 g (60% of theory) of the title compound.

EF: C₁₄H₁₉NO₅; MW: 281.31
MS: 299.1 (MNH₄⁺)
$R_f$=0.29 (petroleum ether/ethyl acetate=1/1)
M.p.: 139-141° C.

Starting from the appropriate starting compounds mentioned below, the following are obtained according to the procedure as in Example E1:

E2. (±)-(1RS,3RS,4SR)-3-(3-Ethoxy-4-methoxy-phenyl)-4-nitrocyclohexanol

E3. (±)-(1RS,3RS,4SR)-3-[3-(1,1-Difluoro-methoxy)-4-methoxy-phenyl]-4-nitrocyclohexanol E4. (±)-(1RS,3RS,4SR)-3-[4-(1,1-Difluoro-methoxy)-3-methoxy-phenyl]-4-nitrocyclohexanol E5. (±)-(1SR,3RS,4SR)-3-(3,4-Dimethoxyphenyl)-4-nitrocyclohexanol 24 g of (±)-(3RS,4SR)-3-(3,4-dimethoxyphenyl)-4-nitrocyclohexanone (compound F1) are dissolved at 60° C. in a mixture consisting of 300 ml of 1,2-dimethoxyethane and 3 ml of methanol and treated portionwise with 1.6 g of sodium borohydride. After 1 h the reaction mixture is cooled to room temperature, 300 ml of water are added and the crude title compound is extracted with ethyl acetate. The organic phase is dried over sodium sulfate and concentrated. The crude title compound is purified by chromatography on silica gel using ethyl acetate/petroleum ether in the ratio 2/1 as eluent. Removal of the solvents of the corresponding eluate fractions yields 11.9 g of the title compound of melting point 119-122° C.

F1. (±)-(3RS,4SR)-3-(3,4-Dimethoxyphenyl)-4-nitrocyclohexanone 90.0 g of 3,4-dimethoxy-ω-nitrostyrene (compound G1), 90 ml of 2-trimethylsilyloxy-1,3-butadiene and 180 ml of abs. toluene are put in an autoclave, where the mixture is stirred at 140° C. for 2 days and then cooled. After addition of 1000 ml of ethyl acetate, 300 ml of a 2 N solution of hydrochloric acid are dropped under stirring. The phases are separated and the aqueous layer is extracted three times with dichloromethane. The combined organic extracts are washed with saturated sodium hydrogencarbonate solution, dried over magnesium sulfate and the solvents are removed under reduced pressure to give 150 g of the crude title compound. Further purification is carried out by chromatography on silica gel using petroleum ether/ethyl acetate in the ratio 1/1 as eluent to give 81.5 g (67% of theory) of the pure title compound.

EF: $C_{14}H_{17}NO_5$; MW: 279.30
MS: 279 ($M^+$), 297.1 ($MNH_4^+$)
$R_f$=0.47 (petroleum ether/ethyl acetate=1/1)
M.p.: 147-148° C.

Starting from the appropriate starting compounds mentioned below, the following are obtained according to the procedure as in Example F1:

F2. (±)-(3RS,4SR)-3-(3-Ethoxy-4-methoxy-phenyl)-4-nitrocyclohexanone

F3. (±)-(3RS,4SR)-3-[3-(1,1-Difluoro-methoxy)-4-methoxy-phenyl]-4-nitrocyclohexanone F4. (±)-(3RS,4SR)-3-[4-(1,1-Difluoro-methoxy)-3-methoxy-phenyl]-4-nitrocyclohexanone G1. 3,4-Dimethoxy-ω-nitrostyrene 207.0 g of 3,4-dimethoxybenzaldehyde, 100.0 g of ammonium acetate and 125 ml of nitromethane are heated to boiling for 3-4 h in 1.0 l of glacial acetic acid. After cooling in an ice bath, the precipitate is filtered off with suction, rinsed with glacial acetic acid and petroleum ether and dried. M.p.: 140-141° C. Yield: 179.0 g.

Starting from art-known starting compounds, the following are obtained according to the procedure as in Example G1:

G2. 3-Ethoxy-4-methoxy-phenyl-ω-nitrostyrene

G3. 3-(1,1-Difluoro-methoxy)-4-methoxy-phenyl-ω-nitrostyrene

G4. 4-(1,1-Difluoro-methoxy)-3-methoxy-phenyl-ω-nitrostyrene

Commercial Utility

The compounds according to the invention have useful pharmacological properties which make them industrially utilizable. As selective cyclic nucleotide phosphodiesterase (PDE) inhibitors (specifically of type 4), they are suitable on the one hand as bronchial therapeutics (for the treatment of airway obstructions on account of their dilating action but also on account of their respiratory rate- or respiratory drive-increasing action) and for the removal of erectile dysfunction on account of their vascular dilating action, but on the other hand especially for the treatment of disorders, in particular of an inflammatory nature, e.g. of the airways (asthma prophylaxis), of the skin, of the intestine, of the eyes, of the CNS and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen free radicals and proteases. In this context, the compounds according to the invention are distinguished by a low toxicity, a good enteral absorption (high bioavailability), a large therapeutic breadth and the absence of significant side effects.

On account of their PDE-inhibiting properties, the compounds according to the invention can be employed in human and veterinary medicine as therapeutics, where they can be used, for example, for the treatment and prophylaxis of the following illnesses: acute and chronic (in particular inflammatory and allergen-induced) airway disorders of varying origin (bronchitis, allergic bronchitis, bronchial asthma, emphysema, COPD); dermatoses (especially of proliferative, inflammatory and allergic type) such as psoriasis (vulgaris), toxic and allergic contact eczema, atopic eczema, seborrhoeic eczema, Lichen simplex, sunburn, pruritus in the anogenital area, alopecia areata, hypertrophic scars, discoid lupus erythematosus, follicular and widespread pyodermias, endogenous and exogenous acne, acne rosacea and other proliferative, inflammatory and allergic skin disorders; disorders which are based on an excessive release of TNF and leukotrienes, for example disorders of the arthritis type (rheumatoid arthritis, rheumatoid spondylitis, osteoarthritis and other arthritic conditions), disorders of the immune system (AIDS, multiple sclerosis), graft versus host reaction, allograft rejections, types of shock (septic shock, endotoxin shock, gram-negative sepsis, toxic shock syndrome and ARDS (adult respiratory distress syndrome)) and also generalized inflammations in the gastrointestinal region (Crohn's disease and ulcerative colitis); disorders which are based on allergic and/or chronic, immunological false reactions in the region of the upper airways (pharynx, nose) and the adjacent regions (paranasal sinuses, eyes), such as allergic rhinitis/sinusitis, chronic rhinitis/sinusitis, allergic conjunctivitis and also nasal polyps; but also disorders of the heart which can be treated by PDE inhibitors, such as cardiac insufficiency, or disorders which can be treated on account of the tissue-relaxant action of the PDE inhibitors, such as, for example, erectile dysfunction or colics of the kidneys and of the ureters in connection with kidney stones. In addition, the compounds of the invention are useful in the treatment of diabetes insipidus and conditions associated with cerebral metabolic inhibition, such as cerebral senility, senile dementia (Alzheimer's disease), memory impairment associated with Parkinson's disease or multiinfarct dementia; and also illnesses of the central nervous system, such as depressions or arteriosclerotic dementia.

The invention further relates to a method for the treatment of mammals, including humans, which are suffering from one of the above mentioned illnesses. The method is characterized in that a therapeutically active and pharmacologically effective and tolerable amount of one or more of the compounds according to the invention is administered to the ill mammal.

The invention further relates to the compounds according to the invention for use in the treatment and/or prophylaxis of illnesses, especially the illnesses mentioned.

The invention also relates to the use of the compounds according to the invention for the production of pharmaceutical compositions which are employed for the treatment and/or prophylaxis of the illnesses mentioned.

The invention also relates to the use of the compounds according to the invention for the production of pharmaceutical compositions for treating disorders which are mediated by phosphodiesterases, in particular PDE4-mediated disorders, such as, for example, those mentioned in the specification of this invention or those which are apparent or known to the skilled person.

The invention furthermore relates to pharmaceutical compositions for the treatment and/or prophylaxis of the illnesses mentioned, which contain one or more of the compounds according to the invention.

Additionally, the invention relates to an article of manufacture, which comprises packaging material and a pharmaceutical agent contained within said packaging material, wherein the pharmaceutical agent is therapeutically effective for antagonizing the effects of the cyclic nucleotide phosphodiesterase of type 4 (PDE4), ameliorating the symptoms of an PDE4-mediated disorder, and wherein the packaging material comprises a label or package insert which indicates that the pharmaceutical agent is useful for preventing or treating PDE4-mediated disorders, and wherein said pharmaceutical agent comprises one or more compounds of formula 1 according to the invention. The packaging material, label and package insert otherwise parallel or resemble what is generally regarded as standard packaging material, labels and package inserts for pharmaceuticals having related utilities.

The pharmaceutical compositions are prepared by processes which are known per se and familiar to the person skilled in the art. As pharmaceutical compositions, the compounds according to the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries or excipients which are suitable for the desired pharmaceutical formulations on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

The administration of the pharmaceutical compositions according to the invention may be performed in any of the generally accepted modes of administration available in the art. Illustrative examples of suitable modes of administration include intravenous, oral, nasal, parenteral, topical, transdermal and rectal delivery. Oral delivery is preferred.

For the treatment of disorders of the respiratory tract, the compounds according to the invention are preferably also administered by inhalation in the form of an aerosol; the aerosol particles of solid, liquid or mixed composition preferably having a diameter of 0.5 to 10 μm, advantageously of 2 to 6 μm.

Aerosol generation can be carried out, for example, by pressure-driven jet atomizers or ultrasonic atomizers, but advantageously by propellant-driven metered aerosols or propellant-free administration of micronized active compounds from inhalation capsules.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparatuses are available with which aerosols of optimum particle size can be generated and administered, using an inhalation technique which is as right as possible for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP 0 505 321), using which an optimal administration of active compound can be achieved.

For the treatment of dermatoses, the compounds according to the invention are in particular administered in the form of those pharmaceutical compositions which are suitable for topical application. For the production of the pharmaceutical compositions, the compounds according to the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by processes known per se. The dosage of the active compounds is carried out in the order of magnitude customary for PDE inhibitors. Topical application forms (such as ointments) for the treatment of dermatoses thus contain the active compounds in a concentration of, for example, 0.1-99%. The dose for administration by inhalation is customarily between 0.01 and 3 mg per day. The customary dose in the case of systemic therapy (p.o. or i.v.) is between 0.003 and 3 mg/kg per day. In another embodiment, the dose for administration by inhalation is between 0.1 and 3 mg per day, and the dose in the case of systemic therapy (p.o. or i.v.) is between 0.03 and 3 mg/kg per day.

Biological Investigations

The second messenger cyclic AMP (CAMP) is well-known for inhibiting inflammatory and immunocompetent cells. The PDE4 isoenzyme is broadly expressed in cells involved in the initiation and propagation of inflammatory diseases (H Tenor and C Schudt, in "Phosphodiesterase Inhibitors", 21-40, "The Handbook of Immunopharmacology", Academic Press, 1996), and its inhibition leads to an increase of the intracellular cAMP concentration and thus to the inhibition of cellular activation (JE Souness et al., Immunopharmacology 47: 127-162, 2000).

The antiinflammatory potential of PDE4 inhibitors in vivo in various animal models has been described (MM Teixeira, TiPS 18: 164-170, 1997). For the investigation of PDE4 inhibition on the cellular level (in vitro), a large variety of proinflammatory responses can be measured. Examples are the superoxide production of neutrophilic (C Schudt et al., Arch Pharmacol 344: 682-690, 1991) or eosinophilic (A Hatzelmann et al., Brit J Pharmacol 114: 821-831, 1995) granulocytes, which can be measured as luminol-enhanced chemiluminescence, or the synthesis of tumor necrosis factor-α in monocytes, macrophages or dendritic cells (Gantner et al., Brit J Pharmacol 121: 221-231, 1997, and Pulmonary Pharmacol Therap 12: 377-386, 1999). In addition, the immunomodulatory potential of PDE4 inhibitors is evident from the inhibition of T-cell responses like cytokine synthesis or proliferation (DM Essayan, Biochem Pharmacol 57: 965-973, 1999). Substances which inhibit the secretion of the aforementioned proinflammatory mediators are those which inhibit PDE4. PDE4 inhibition by the compounds according to the invention is thus a central indicator for the suppression of inflammatory processes.

Methods for Measuring Inhibition of PDE4 Activity

Method a:

PDE4 activity was determined as described by Thompson et al. (Adv Cycl Nucl Res 10: 69-92, 1979) with some modifications (Bauer and Schwabe, Naunyn-Schmiedeberg's Arch Pharmacol 311: 193-198, 1980). At a final assay volume of 200 µl (96 well microtiter plates) the assay mixture contained 20 mM Tris (pH 7.4), 5 mM MgCl$_2$, 0.5 µM cAMP, [$^3$H]cAMP (about 30,000 cpm/assay), the test compound and an aliquot of cytosol from human neutrophils which mainly contains PDE4 activity as described by Schudt et al. (Naunyn-Schmiedeberg's Arch Pharmacol 344: 682-690, 1991); the PDE3-specific inhibitor Motapizone (1 µM) was included to suppress PDE3 activity originating from contaminating platelets. Serial dilutions of the compounds were prepared in DMSO and further diluted 1:100 (v/v) in the assays to obtain the desired final concentrations of the inhibitors at a DMSO concentration of 1% (v/v) which by itself only slightly affected PDE4 activity.

After preincubation for 5 min at 37° C., the reaction was started by the addition of substrate (cAMP) and the assays were incubated for further 15 min at 37° C. 50 µl of 0.2 N HCl was added to stop the reaction and the assays were left on ice for about 10 min. Following incubation with 25 µg 5'-nucleotidase (Crotalus atrox snake venom) for 10 min at 37° C., the assays were loaded on QAE Sephadex A-25 (1 ml bed volume). The columns were eluted with 2 ml of 30 mM ammonium formiate (pH 6.0) and the eluate was counted for radioactivity. Results were corrected for blank values (measured in the presence of denatured protein) which were below 5% of total radioactivity. The amount of cyclic nucleotides hydrolyzed did not exceed 30% of the original substrate concentration. The IC$_{50}$-values for the compounds according to the invention for the inhibition of the PDE4 activity were determined from the concentration-inhibition curves by nonlinear-regression.

Method b:

The PDE4B2 (GB no. M97515) was a gift of Prof. M. Conti (Stanford University, USA). It was amplified from the original plasmid (pCMV5) via PCR with primers Rb9 (5'-GCCAGCGTGCAAATAATGAAGG-3') and Rb10 (5'-AGAGGGGGATTATGTATCCAC-3') and cloned into the pCR-Bac vector (Invitrogen, Groningen, NL).

The recombinant baculovirus was prepared by means of homologous recombination in SF9 insect cells. The expression plasmid was cotransfected with Bac-N-Blue (Invitrogen, Groningen, NL) or Baculo-Gold DNA (Pharmingen, Hamburg) using a standard protocol (Pharmingen, Hamburg). Wt virus-free recombinant virus supernatant was selected using plaque assay methods. After that, high-titre virus supernatant was prepared by amplifying 3 times. PDE was expressed in SF21 cells by infecting 2×10$^6$ cells/ml with an MOI (multiplicity of infection) between 1 and 10 in serum-free SF900 medium (Life Technologies, Paisley, UK). The cells were cultured at 28° C. for 48-72 hours, after which they were pelleted for 5-10 min at 1000 g and 4° C.

The SF21 insect cells were resuspended, at a concentration of approx. 10$^7$ cells/ml, in ice-cold (4° C.) homogenization buffer (20 mM Tris, pH 8.2, containing the following additions: 140 mM NaCl, 3.8 mM KCl, 1 mM EGTA, 1 mM MgCl$_2$, 10 mM β-mercaptoethanol, 2 mM benzamidine, 0.4 mM Pefablock, 10 µM leupeptin, 10 µM pepstatin A, 5 µM trypsin inhibitor) and disrupted by ultrasonication. The homogenate was then centrifuged for 10 min at 1000×g and the supernatant was stored at −80° C. until subsequent use (see below). The protein content was determined by the Bradford method (BioRad, Munich) using BSA as the standard.

PDE4B2 activity is inhibited by the said compounds in a modified SPA (scintillation proximity assay) test, supplied by Amersham Biosciences (see procedural instructions "phosphodiesterase [3H]cAMP SPA enzyme assay, code TRKQ 7090"), carried out in 96-well microtiter plates (MTP's). The test volume is 100 µl and contains 20 mM Tris buffer (pH 7.4), 0.1 mg of BSA (bovine serum albumin)/ml, 5 mM Mg$^{2+}$, 0.5 µM cAMP (including about 50,000 cpm of [3H]cAMP), 1 µl of the respective substance dilution in DMSO and sufficient recombinant PDE (1000×g supernatant, see above) to ensure that 10-20% of the cAMP is converted under the said experimental conditions. The final concentration of DMSO in the assay (1% v/v) does not substantially affect the activity of the PDE investigated. After a preincubation of 5 min at 37° C., the reaction is started by adding the substrate (cAMP) and the assay is incubated for a further 15 min; after that, it is stopped by adding SPA beads (50 µl). In accordance with the manufacturer's instructions, the SPA beads had previously been resuspended in water, but were then diluted 1:3 (v/v) in water; the diluted solution also contains 3 mM IBMX to ensure a complete PDE activity stop. After the beads have been sedimented (>30 min), the MTP's are analyzed in commercially available luminescence detection devices. The corresponding IC$_{50}$ values of the compounds for the inhibition of PDE activity are determined from the concentration-effect curves by means of non-linear regression.

The inhibitory values determined for the compounds according to the invention follow from the following table A, in which the numbers of the compounds correspond to the numbers of the examples.

The inhibitory values of the compounds 5-13, 44, 65 and 66 have been determined according to Method a. The inhibitory values of the compounds 43, 45, 46, 48-64 and 76 have been determined according to Method b.

TABLE A

Inhibition of the PDE4 activity

| Compound | −log IC$_{50}$ |
|---|---|
| 5 | 7.09 |
| 6 | 7.26 |
| 7 | 8.98 |
| 8 | 9.21 |
| 9 | 7.13 |
| 10 | 8.71 |
| 11 | 9.11 |
| 12 | 8.25 |
| 13 | 8.12 |
| 43 | The inhibitory |
| 44 | values of |
| 45 | these mentioned |
| 46 | Examples |
| 48 | lie in the |
| 49 | range from |
| 50 | 8.22 to 9.74 |
| 51 | |
| 52 | |

TABLE A-continued

Inhibition of the PDE4 activity

| Compound | $-\log IC_{50}$ |
|---|---|
| 53 | |
| 54 | |
| 55 | |
| 56 | |
| 57 | |
| 58 | |
| 59 | |
| 60 | |
| 61 | |
| 62 | |
| 63 | |
| 64 | |
| 65 | |
| 66 | |
| 76 | |

The invention claimed is:

1. A method for treating dermatoses in a patient comprising administering to said patient a therapeutically effective amount of a compound of the formula I

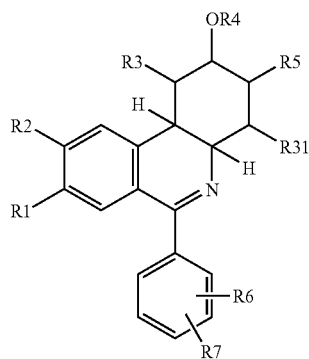

in which
R1 is hydroxyl, 1-4C-alkoxy, 3-7C-cycloalkoxy, 3-7C-cycloalkyl methoxy, or completely or predominantly fluorine-substituted 1-4C-alkoxy,
R2 is hydroxyl, 1-4C-alkoxy, 3-7C-cycloalkoxy, 3-7C-cycloalkyl methoxy, or completely or predominantly fluorine-substituted 1-4C-alkoxy,
or in which
R1 and R2 together are a 1-2C-alkylenedioxy group,
R3 is hydrogen or 1-4C-alkyl,
R31 is hydrogen or 1-4C-alkyl,
R4 is hydrogen, 1-4C-alkyl, completely or predominantly fluorine-substituted 1-4C-alkyl, 1-4C-alkoxy-1-4C-alkyl, hydroxy-2-4C-alkyl or 1-7C-alkylcarbonyl,
R5 is hydrogen or 1-4C-alkyl,
R6 is hydrogen, 1-4C-alkyl, trifluoromethyl, 1-4C-alkoxy, completely or predominantly fluorine-substituted 1-4C-alkoxy, 3-7C-cycloalkoxy, 3-7C-cycloalkylmethoxy, halogen, nitro, cyano, hydroxyl, 1-4C-alkylcarbony-loxy, amino, mono- or di-1-4C-alkylamino, phenyl, phenyl-1-4C-alkyl, 1-4C-alkylcarbonylamino, phenoxy or C(O)OR61, wherein
R61 is hydrogen, 1-7C-alkyl, 3-7C-cycloalkyl or 3-7C-cycloalkylmethyl,
R7 is hydrogen, 1-4C-alkyl, hydroxyl, halogen, 1-4C-alkoxy, completely or predominantly fluorine-substituted 1-4C-alkoxy, 3-7C-cycloalkoxy, 3-7C-cycloalkylmethoxy or C(O)OR61,
or a pharmaceutically acceptable salt of this compound, a pharmaceutically acceptable N-oxide of this compound, or a salt of said N-oxide, wherein the dermatoses is selected from the group consisting of psoriasis and atopic eczema.

2. The method according to claim 1, in which
R1 is hydroxyl, 1-4C-alkoxy, 3-7C-cycloalkoxy, 3-7C-cycloalkylmethoxy or completely or predominantly fluorine-substituted 1-4C-alkoxy,
R2 is hydroxyl, 1-4C-alkoxy, 3-7C-cycloalkoxy, 3-7C-cycloalkylmethoxy or completely or predominantly fluorine-substituted 1-4C-alkoxy, or in which
R1 and R2 together are a 1-2C-alkylenedioxy group,
R3 is hydrogen or 1-4C-alkyl,
R31 is hydrogen or 1-4C-alkyl,
R4 is hydrogen, 1-4C-alkyl, completely or predominantly fluorine-substituted 1-4C-alkyl, 1-4C-alkoxy-1-4C-alkyl, hydroxy-2-4C-alkyl or 1-7C-alkylcarbonyl,
R5 is hydrogen or 1-4C-alkyl,
R6 is hydrogen, 1-4C-alkyl, trifluoromethyl, 1-4C-alkoxy, completely or predominantly fluorine-substituted 1-4C-alkoxy, 3-7C-cycloalkoxy, 3-7C-cycloalkylmethoxy, halogen, nitro, cyano, hydroxyl, 1-4C-alkylcarbonyloxy, amino, mono- or di-1-4C-alkylamino, phenyl, phenyl-1-4C-alkyl, 1-4C-alkylcarbonylamino or C(O)OR61, wherein
R61 is hydrogen, 1-7C-alkyl, 3-7C-cycloalkyl or 3-7C-cycloalkylmethyl,
R7 is hydrogen, 1-4C-alkyl, hydroxyl, halogen, 1-4C-alkoxy, completely or predominantly fluorine-substituted 1-4C-alkoxy, 3-7C-cycloalkoxy, 3-7C-cycloalkylmethoxy or C(O)OR61, or a pharmaceutically acceptable salt of this compound, an N-oxide of this compound, or a salt of an N-oxide of this compound.

3. The method according to claim 1, in which
R1 is 1-2C-alkoxy, 3-5C-cycloalkoxy, 3-5C-cycloalkyl methoxy, or completely or predominantly fluorine-substituted 1-2C-alkoxy,
R2 is 1-2C-alkoxy, 3-5C-cycloalkoxy, 3-5C-cycloalkylmethoxy, or completely or predominantly fluorine-substituted 1-2C-alkoxy,
R3 is hydrogen,
R31 is hydrogen,
R4 is hydrogen, 1-4C-alkyl, 1-2C-alkoxy-2-4C-alkyl or 1-7C-alkylcarbonyl,
R5 is hydrogen,
R6 is 1-4C-alkyl, 1-4C-alkoxy, completely or predominantly fluorine-substituted 1-4C-alkoxy, 3-7C-cycloalkyl methoxy, halogen, nitro, cyano, hydroxyl, 1-4C-alkylcarbonyloxy, mono- or di-1-4C-alkylamino, 1-4C-alkylcarbonylamino, phenoxy or C(O)OR61, wherein
R61 is hydrogen or 1-7C-alkyl,
R7 is hydrogen, halogen, 1-4C-alkoxy, completely or predominantly fluorine-substituted 1-4C-alkoxy or 3-7C-cycloalkylmethoxy,
or a pharmaceutically acceptable salt of this compound, an N-oxide of this compound, or a salt of an N-oxide of this compound.

4. The method according to claim 1, in which
R1 is 1-2C-alkoxy, or completely or predominantly fluorine-substituted 1-2C-alkoxy,
R2 is 1-2C-alkoxy, or completely or predominantly fluorine-substituted 1-2C-alkoxy,
R3 is hydrogen,
R31 is hydrogen,
R4 is hydrogen, 1-4C-alkyl, 1-2C-alkoxyethyl or 1-7C-alkylcarbonyl,
R5 is hydrogen,
R6 is 1-4C-alkyl, 1-4C-alkoxy, completely or predominantly fluorine-substituted 1-4C-alkoxy, 3-7C-cycloalkylmethoxy, halogen, nitro, cyano, hydroxyl, 1-4C-alkylcarbonyloxy, mono- or di-1-4C-alkylamino, 1-4C-alkylcarbonylamino, phenoxy or C(O)OR61, wherein
R61 is hydrogen or 1-7C-alkyl,
R7 is hydrogen, halogen, 1-4C-alkoxy, completely or predominantly fluorine-substituted 1-4C-alkoxy, or 3-7C-cycloalkylmethoxy,
or a pharmaceutically acceptable salt of this compound, an N-oxide of this compound, or a salt of an N-oxide of this compound.

5. The method according to claim 1, in which
R1 is ethoxy, and
R2 is methoxy or difluoromethoxy,
or
R1 is methoxy or difluoromethoxy, and
R2 is methoxy, difluoromethoxy or ethoxy,
or
R1 is difluoromethoxy, and
R2 is methoxy or ethoxy,
or
R1 is methoxy, and
R2 is ethoxy or difluoromethoxy,
R3 is hydrogen,
R31 is hydrogen,
R4 is hydrogen, 1-4C-alkyl, 1-2C-alkoxyethyl or 1-7C-alkylcarbonyl,
R5 is hydrogen,
R6 is 1-4C-alkyl, 1-4C-alkoxy, completely or predominantly fluorine-substituted 1-4C-alkoxy, 3-7C-cycloalkylmethoxy, halogen, nitro, cyano, hydroxyl, 1-4C-alkylcarbonyloxy, mono- or di-1-4C-alkylamino, 1-4C-alkylcarbonylamino, phenoxy or C(O)OR61, wherein
R61 is hydrogen or 1-7C-alkyl,
R7 is hydrogen, halogen, 1-4C-alkoxy, completely or predominantly fluorine-substituted 1-4C-alkoxy, or 3-7C-cycloalkyl methoxy,
or a pharmaceutically acceptable salt of this compound, an N-oxide of this compound, or a salt of an N-oxide of this compound.

6. The method according to claim 1, in which
R1 is methoxy or difluoromethoxy,
R2 is methoxy, difluoromethoxy or ethoxy,
R3 is hydrogen,
R31 is hydrogen,
R4 is hydrogen, methyl, ethyl, methoxyethyl or acetyl,
R5 is hydrogen,
R6 is methyl, methoxy, ethoxy, propoxy, butoxy, difluoromethoxy, trifluoromethoxy, 1,1,2,2-tetrafluoroethoxy, cyclopropylmethoxy, fluorine, chlorine, bromine, nitro, cyano, hydroxyl, acetoxy, dimethylamino, acetamido, phenoxy or C(O)OR61, wherein
R61 is hydrogen or methyl,
R7 is hydrogen, fluorine, methoxy, ethoxy, propoxy, butoxy, difluoromethoxy or cyclopropylmethoxy,
or a pharmaceutically acceptable salt of this compound, an N-oxide of this compound, or a salt of an N-oxide of this compound.

7. The method according to claim 1, in which
R1 is methoxy, and
R2 is methoxy,
or
R1 is difluoromethoxy, and
R2 is methoxy,
or
R1 is methoxy, and
R2 is ethoxy or difluoromethoxy,
R3 is hydrogen,
R31 is hydrogen,
R4 is hydrogen, methyl, ethyl, methoxyethyl or acetyl,
R5 is hydrogen, R6 is methyl, methoxy, ethoxy, propoxy, butoxy, difluoromethoxy, trifluoromethoxy, 1,1,2,2-tetrafluoroethoxy, cyclopropylmethoxy, fluorine, chlorine, bromine, nitro, cyano, hydroxyl, acetoxy, dimethylamino, acetamido, phenoxy or C(O)OR61, wherein R61 is hydrogen or methyl, R7 is hydrogen, fluorine, methoxy, difluoromethoxy or cyclopropylmethoxy, or a pharmaceutically acceptable salt of this compound, an N-oxide of this compound, or a salt of an N-oxide of this compound.

8. The method according to claim 1, in which

R1 is methoxy,

R2 is methoxy,

R3 is hydrogen,

R31 is hydrogen,

R4 is hydrogen or acetyl,

R5 is hydrogen,

R6 is methoxy, cyclopropylmethoxy, nitro, dimethylamino or C(O)OR61, wherein

R61 is hydrogen or methyl,

R7 is hydrogen, methoxy or cyclopropylmethoxy, or a pharmaceutically acceptable salt of this compound, an N-oxide of this compound, or a salt of an N-oxide of this compound.

9. The method according to claim 1, in which the compound is selected from the group consisting of (±)-acetic acid (2RS,4a RS,10bRS)-6-(3,4-bis-cyclopropylmethoxy-phenyl)-8,9-dimethoxy-(1,2,3,4,4a,10b)-hexahydrophenanthridin-2-yl ester, (±)-acetic acid (2RS,4a RS,10bRS)-6-(4-methoxycarbonylphenyl)-8,9-dimethoxy-(1,2,3,4,4a,10b)-hexahydrophenanthridin-2-yl ester, (±)-acetic acid (2RS,4aRS,10bRS)-6-(4-dimethylaminophenyl)-8,9-dimethoxy-(1,2,3,4,4a,10b)-hexahydrophenanthridin-2-yl ester, (±)-acetic acid (2RS,4aRS,10bRS)-6-(3,4-dimethoxyphenyl)-8,9-dimethoxy-(1,2,3,4,4a,10b)-hexahydrophenanthridin-2-yl ester, (±)-acetic acid (2RS,4aRS,10bRS)-6-(4-nitrophenyl)-8,9-dimethoxy-(1,2,3,4,4a,10b)-hexahydrophenanthridin-2-yl ester, (±)-acetic acid (2RS,4aRS,10bRS)-6-(3,4-bis-cyclopropyl-methoxyphenyl)-8,9-dimethoxy-(1,2,3,4,4a,10b)-hexahydro-phenanthridin-2-yl ester, (±)-(2RS,4aRS,10bRS)-6-(3,4-bis-cyclopropylmethoxyphenyl)-8,9-dimethoxy-(1,2,3,4,4a,10b)-hexahydrophenanthridin-2-ol, (±)-(2RS,4aRS,10bRS)-6-(4-methoxycarbonylphenyl)-8,9-dimethoxy-(1,2,3,4,4a,10b)-hexahydrophenanthridin-2-ol, (±)-(2RS,4aRS,10bRS)-6-(4-dimethylaminophenyl)-8,9-dimethoxy-(1,2,3,4,4a,10b)-hexahydrophenanthridin-2-ol, (±)-(2RS,4aRS,10bRS)-6-(3,4-dimethoxyphenyl)-8,9-dimethoxy-(1,2,3,4,4a,10b)-hexahydrophenanthridin-2-ol, (±)-(2RS,4aRS,10bRS)-6-(4-nitrophenyl)-8,9-dimethoxy-(1,2,3,4,4a,10b)-hexahydrophenanthridin-2-ol, (±)-(2RS,4aRS,10bRS)-6-(4-carboxyphenyl)-8,9-dimethoxy-(1,2,3,4,4a,10b)-hexahydrophenanthridin-2-ol, (±)-(2RS,4aRS,10bRS)-6-(3,4-bis-cyclopropylmethoxyphenyl)-8,9-dimethoxy-(1,2,3,4,4a,10b)-hexahydrophenanthridin-2-ol, (±)-acetic acid (2RS,4aRS,10bRS)-6-(4-butoxy-phenyl)-8,9-dimethoxy-1,2,3,4,4a,10b-hexahydrophenanthridin-2-yl ester, (±)-acetic acid (2RS,4aRS,10bRS)-8,9-dimethoxy-6-(4-methoxy-phenyl)-1,2,3,4,4a,10b-hexahydrophenanthridin-2-yl ester, (±)-acetic acid (2RS,4aRS,10bRS)-6-(4-cyano-phenyl)-8,9-dimethoxy-1,2,3,4,4a,10b-hexahydrophenanthridin-2-yl ester, (±)-acetic acid 4-((2RS,4aRS,10bRS)-2-acetoxy-8,9-dimethoxy-1,2,3,4,4a,10b-hexahydrophenanthridin-6-yl)-phenyl ester, (±)-acetic acid (2RS,4aRS,10bRS)-6-(4-acetylamino-phenyl)-8,9-dimethoxy-1,2,3,4,4a,10b-hexahydrophenanthridin-2-yl ester, (±)-acetic acid (2RS,4aRS,10bRS)-6-(4-chloro-phenyl)-8,9-dimethoxy-1,2,3,4,4a,10b-hexahydrophenanthridin-2-yl ester, (±)-acetic acid (2RS,4aRS,10bRS)-6-(2-chloro-phenyl)-8,9-dimethoxy-1,2,3,4,4a,10b-hexahydrophenanthridin-2-yl ester, (±)-acetic acid (2RS,4aRS,10bRS)-8,9-dimethoxy-6-(4-methoxy-3-propoxy-phenyl)-1,2,3,4,4a,10b-hexahydrophenanthridin-2-yl ester, (±)-acetic acid (2RS,4aRS,10bRS)-8,9-dimethoxy-6-p-tolyl-1,2,3,4,4a,10b-hexahydrophenanthridin-2-yl ester, (±)-4-((2RS,4aRS,10bRS)-2-acetoxy-9-ethoxy-8-methoxy-1,2,3,4,4a,10b-hexahydrophenanthridin-6-yl)-benzoic acid methyl ester, (±)-acetic acid (2RS,4aRS,10bRS)-9-ethoxy-6-(4-fluoro-phenyl)-8-methoxy-1,2,3,4,4a,10b-hexahydrophenanthridin-2-yl ester, (±)-acetic acid (2RS,4aRS,10bRS)-6-(4-cyano-phenyl)-9-ethoxy-8-methoxy-1,2,3,4,4a,10b-hexahydro-phenanthridin-2-yl ester, (±)-acetic acid (2 RS,4aRS,10bRS)-6-(3-cyclopropylmethoxy-4-ethoxy-phenyl)-9-ethoxy-8-methoxy-1,2,3,4,4a,10b-hexahydro-phenanthridin-2-yl ester, (±)-acetic acid (2RS,4aRS,10bRS)-6-[3-cyclopropyl methoxy-4-(1,1-difluoro-methoxy)phenyl]-9-ethoxy-8-methoxy-1,2,3,4,4a,10b-hexahydro-phenanthridin-2-yl ester, (±)-acetic acid (2RS,4aRS,10bRS)-6-[3,4-bis(1,1-difluoro-methoxy)-phenyl]-9-ethoxy-8-methoxy-1,2,3,4,4a, 10b-hexahydro-phenanthridin-2-yl ester, (±)-acetic acid (2RS,4a RS,10bRS)-6-[3'-(1,1-difluoromethoxy)-phenyl]-9-ethoxy-8-methoxy-1,2,3,4,4a,10b-hexahydro-phenanthridin-2-yl ester, (±)-acetic acid (2RS,4a RS,10bRS)-9-ethoxy-8-methoxy-6-[4-(1,1,2,2-tetrafluoro-ethoxy)-phenyl]-1,2,3,4,4a,10b-hexahydro-phenanthridin-2-yl ester, (±)-acetic acid (2RS,4aRS,10bRS)-9-ethoxy-8-methoxy-6-(4-trifluoromethoxy-phenyl)-1,2,3,4,4a,10b-hexahydro-phenanthridin-2-yl ester, (±)-acetic acid (2RS,4aRS,10bRS)-9-ethoxy-6-(3-fluoro-4-methoxy-phenyl)-8-methoxy-1,2,3,4,4a,10b-hexahydro-phenanthridin-2-yl ester, (±)-acetic acid (2 RS,4a RS,10bRS)-6-(3,4-difluoro-phenyl)-9-ethoxy-8-methoxy-1,2,3,4,4a,10b-hexahydro-phenanthridin-2-yl ester, (±)-acetic acid (2RS,4aRS,10bRS)-9-ethoxy-6-(3-fluoro-phenyl)-8-methoxy-1,2,3,4,4a,10b-hexahydro-phenanthridin-2-yl ester, (±)-acetic acid (2RS,4aRS,10bRS)-6-(4-bromo-phenyl)-9-ethoxy-8-methoxy-1,2,3,4,4a,10b-hexahydro-phenanthridin-2-yl ester, (±)-acetic acid (2RS,4aRS,10bRS)-6-[4-(1,1-difluoro-methoxy)-phenyl]-8,9-dimethoxy-1,2,3,4,4a,10b-hexahydro-phenanthridin-2-yl ester, (±)-acetic acid (2RS,4aRS,10bRS)-8,9-dimethoxy-6-(4-phenoxy-phenyl)-1,2,3,4,4a,10b-hexahydro-phenanthridin-2-yl ester, (±)-acetic acid (2RS,4aRS,10bRS)-6-(4-fluoro-phenyl)-8,9-dimethoxy-1,2,3,4,4a,10b-hexahydro-phenanthridin-2-yl ester, (±)-acetic acid (2RS,4aRS,10bRS)-6-[3,4-bis-(1,1-difluoro-methoxy)-phenyl]-8-(1,1-difluoro-methoxy)-9-methoxy-1,2,3,4,4a,10b-hexahydro-phenanthridin-2-yl ester, (±)-acetic acid (2RS,4aRS,10bRS)-6-(4-cyano-phenyl)-8-(1,1-difluoro-methoxy)-9-methoxy-1,2,3,4,4a,10b-hexahydro-phenanthridin-2-yl ester, (±)-4-[(2 RS,4a RS,10bRS)-2-acetoxy-8-(1,1-difluoro-methoxy)-9-methoxy-1,2,3,4,4a,10b-hexahydro-phenanthridin-6-yl]-benzoic acid methyl ester, (±)-4-[(2RS,4aRS,10bRS)-2-acetoxy-9-(1,1-difluoro-methoxy)-8-methoxy-1,2,3,4,4a,10b-hexahydro-phenanthridin-6-yl]-benzoic acid methyl ester, (±)-(2RS,4aRS,10bRS)-6-(4-butoxy-phenyl)-8,9-dimethoxy-1,2,3,4,4a,10b-hexahydro-phenanthridin-2-ol, (±)-(2RS,4aRS,10bRS)-6-(4-fluoro-phenyl)-8,9-dimethoxy-1,2,3,4,4a,10b-hexahydro-phenanthridin-2-ol, (±)-N-[4-((2RS,4aRS,10bRS)-2-hydroxy-8,9-dimethoxy-1,2,3,4,4a,10b-hexahydro-phenanthridin-6-yl)-phenyl]-acetamide, (±)-(2RS,4aRS,10bRS)-6-(4-chloro-phenyl)-8,9-dimethoxy-1,2,3,4,4a,10b-hexahydro-phenanthridin-2-ol, (±)-(2RS,4aRS,10bRS)-6-(2-chloro-phenyl)-8,9-dimethoxy-1,2,3,4,4a,10b-hexahydro-phenanthridin-2-ol, (±)-(2RS,4aRS,10bRS)-8,9-dimethoxy-6-(4-methoxy-3-propoxy-phenyl)-1,2,3,4,4a,10b-hexahydro-phenanthridin-2-ol, (±)-(2RS,4aRS,10bRS)-6-[4-(1,1-difluoro-methoxy)-phenyl]-8,9-dimethoxy-1,2,3,4,4a,10b-hexahydro-phenanthridin-2-ol, (±)-4-((2 RS,4aRS,10bRS)-9-ethoxy-2-hydroxy-8-methoxy-1,2,3,4,4a, 10b-hexahydro-phenanthridin-6-yl)-benzoic acid methyl ester, (±)-(2RS,4aRS,10bRS)-9-ethoxy-6-(4-fluoro-phenyl)-8-methoxy-1,2,3,4,4a,10b-hexahydro-phenanthridin-2-ol, (±)-4-((2 RS,4aRS,10bRS)-9-ethoxy-2-hydroxy-8-methoxy-1,2,3,4,4a,10b-hexahydro-phenanthridin-6-yl)-benzonitrile, (±)-(2RS,4aRS,10bRS)-6-(3-cyclopropyl methoxy-4-ethoxy-phenyl)-9-ethoxy-8-methoxy-1,2,3,4,4a,10b-hexahydro-phenanthridin-2-ol, (±)-(2RS,4aRS,10bRS)-6-[3-cyclopropylmethoxy-4-(1,1-difluoro-methoxy)-phenyl]-9-ethoxy-8-methoxy-1,2,3,4,4a,10b-hexahydro-phenanthridin-2-ol, (±)-(2RS,4aRS,10bRS)-6-[3,4-bis-(1,1-difluoro-methoxy)-phenyl]-9-ethoxy-8-methoxy-1,2,3,4,4a,10b-hexahydro-phenanthridin-2-ol, (±)-(2RS,4aRS,10bRS)-6-[3-(1,1-difluoro-methoxy)-phenyl]-9-ethoxy-8-methoxy-1,2,3,4,4a,10b-hexahydro-phenanthridin-2-ol, (±)-(2RS,4a RS,10bRS)-9-ethoxy-8-methoxy-6-[4-(1,1,2,2-tetrafluoro-ethoxy)-phenyl]-1,2,3,4,4a,10b-hexahydro-phenanthridin-2-ol, (±)-(2RS,4aRS,10bRS)-9-ethoxy-8-methoxy-6-(4-trifluoromethyl-phenyl)-1,2,3,4,4a,10b-hexahydro-phenanthridin-2-ol, (±)-(2RS,4aRS,10bRS)-9-ethoxy-6-(3-fluoro-4-methoxy-phenyl)-8-methoxy-1,2,3,4,4a,10b-hexahydro-phenanthridin-2-ol, (±)-(2RS,4aRS,10bRS)-6-(3,4-difluoro-phenyl)-9-ethoxy-8-methoxy-1,2,3,4,4a,10b-hexahydro-phenanthridin-2-ol, (±)-(2RS,4aRS,10bRS)-9-ethoxy-6-(3-fluoro-phenyl)-8-methoxy-1,2,3,4,4a,10b-hexahydro-phenanthridin-2-ol, (±)-(2RS,4aRS,10bRS)-6-(4-bromo-phenyl)-9-ethoxy-8-methoxy-1,2,3,4,4a,10b-hexahydro-phenanthridin-2-ol, (±)-(2RS,4aRS,10bRS)-8,9-dimethoxy-6-p-tolyl-1,2,3,4,4a,10b-hexahydro-phenanthridin-2-ol, (±)-(2RS,4aRS,10bRS)-8,9-dimethoxy-6-(4-phenoxy-phenyl)-1,2,3,4,4a,10b-hexahydro-phenanthridin-2-ol, (±)-(2RS,4aRS,10bRS)-8,9-dimethoxy-6-(4-methoxy-phenyl)-1,2,3,4,4a,10b-hexahydro-phenanthridin-2-ol, (±)-4-((2RS,4aRS,10bRS)-2-hydroxy-8,9-dimethoxy-1,2,3,4,4a,10b-hexahydro-phenanthridin-6-yl)-benzonitrile, (±)-(2RS,4aRS,10bRS)-6-[3,4-bis-(1,1-difluoro-methoxy)-phenyl]-8-(1,1-difluoro-methoxy)-9-methoxy-1,2,3,4,4a,10b-hexahydro-phenanthridin-2-ol, (±)-4-[(2RS,4aRS,10bRS)-8-(1,1-difluoro-methoxy)-2-hydroxy-9-methoxy-1,2,3,4,4a,10b-hexahydro-phenanthridin-6-yl]-benzonitrile, (±)-4-[(2RS,4aRS,10bRS)-8-(1,1-difluoro-methoxy)-2-hydroxy-9-methoxy-1,2,3,4,4a,10b-hexahydro-phenanthridin-6-yl]-benzoic acid methyl ester, (±)-4-[(2RS,4aRS,10bRS)-9-(1,1-difluoro-methoxy)-2-hydroxy-8-methoxy-1,2,3,4,4a,10b-hexahydro-phenanthridin-6-yl]-benzoic acid methyl ester, (±)-acetic acid (2RS,4aRS,10bRS)-6-(4-hydroxy-phenyl)-8,9-dimethoxy-1,2,3,4,4a,10b-hexahydro-phenanthridin-2-yl ester, (±)-4-((2RS,4aRS,10bRS)-2-acetoxy-8,9-dimethoxy-1,2,3,4,4a,10b-hexahydro-phenanthridin-6-yl)-benzoic acid hydrochloride, (±)-4-((2RS,4aRS,10bRS)-2-acetoxy-9-(1,1-difluoro-methoxy)-8-methoxy-1,2,3,4,4a,10b-hexahydro-phenanthridin-6-yl)-benzoic acid, (±)-(2RS,4aRS,10bRS)-6-(3,4-bis-cyclopropylmethoxy-phenyl)-2,8,9-trimethoxy-1,2,3,4,4a,10b-hexahydro-phenanthridine, (±)-(2RS,4aRS,10bRS)-6-(3,4-bis-cyclopropyl methoxy-phenyl)-2-ethoxy-8,9-dimethoxy-1,2,3,4,4a,10b-hexahydro-phenanthridine, (±)-(2RS,4aRS,10bRS)-6-(3,4-bis-cyclopropylmethoxy-phenyl)-8,9-dimethoxy-2-(2-methoxy-ethoxy)-1,2,3,4,4a,10b-hexahydro-phenanthridine, the pharmaceutically acceptable salts of these compounds, the N-oxides of these compounds, and the salts of the N-oxides of these compounds.

10. The method according to claim 1, in which the hydrogen atoms in positions 4a and 10b are in the cis position relative to one another, or a pharmaceutically acceptable salt of this compound, an N-oxide of this compound, or a salt of an N-oxide of this compound.

11. The method according to claim 1, in which the compound has, with respect to the positions 4a and 10b, the configuration shown in formula I*:

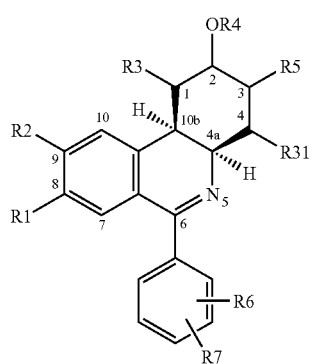

(I*)

or a pharmaceutically acceptable salt of this compound, an N-oxide of this compound, or a salt of an N-oxide of this compound.

12. The method according to claim 1, in which the compound has, with respect to the positions 2, 4a and 10b, the configuration shown either in formula I, I* or I****:

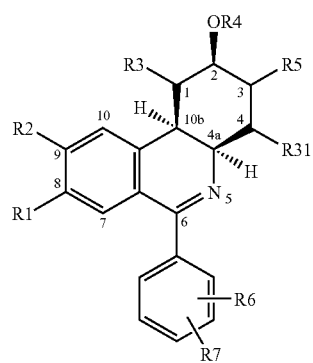

(I**)

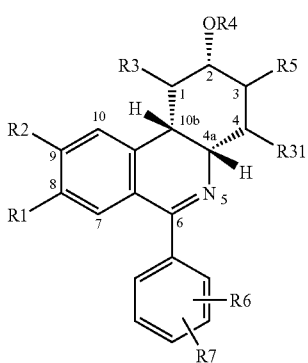

(I***)

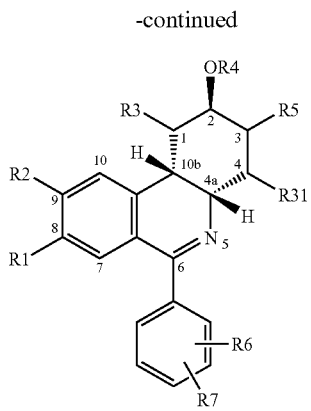

(I****)

or a pharmaceutically acceptable salt of this compound, an N-oxide of this compound, or a salt of an N-oxide of this compound.

13. The method according to claim 1, in which the compound has, with respect to the position 2, 4a, and 10b, the configuration shown in formula I*****:

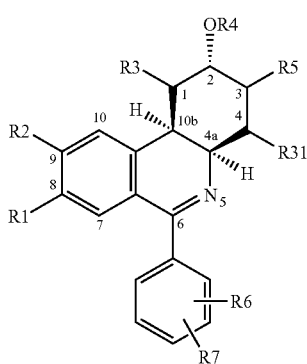

(I*****)

or a pharmaceutically acceptable salt of this compound, an N-oxide of this compound, or a salt of an N-oxide of this compound.

* * * * *

SEQUENCE LISTING

<160> NUMBER OF SEQ ID NOS: 2

<210> SEQ ID NO 1
<211> LENGTH: 22
<212> TYPE: DNA
<213> ORGANISM: Homo sapiens

<400> SEQUENCE: 1
gccagcgtgc aaataatgaa gg         22

<210> SEQ ID NO 2
<211> LENGTH: 21
<212> TYPE: DNA
<213> ORGANISM: Homo sapiens

<400> SEQUENCE: 2
agagggggat tatgtatcca c          21